United States Patent
Firstenberg et al.

(10) Patent No.: US 10,342,684 B2
(45) Date of Patent: Jul. 9, 2019

(54) ANTI-MIGRATION MICROPATTERNED STENT COATING

(71) Applicant: BOSTON SCIENTIFIC SCIMED, INC., Maple Grove, MN (US)

(72) Inventors: Laura Elizabeth Firstenberg, Boston, MA (US); Sean P. Fleury, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 26 days.

(21) Appl. No.: 15/340,465

(22) Filed: Nov. 1, 2016

(65) Prior Publication Data

US 2017/0056213 A1    Mar. 2, 2017

Related U.S. Application Data

(63) Continuation of application No. 14/210,979, filed on Mar. 14, 2014, now Pat. No. 9,517,122.

(Continued)

(51) Int. Cl.
*A61F 2/848* (2013.01)
*A61F 2/06* (2013.01)
(Continued)

(52) U.S. Cl.
CPC ............ *A61F 2/848* (2013.01); *A61F 2/0077* (2013.01); *A61F 2/04* (2013.01); *A61F 2/06* (2013.01);
(Continued)

(58) Field of Classification Search
CPC .......... A61F 2/82; A61F 2/848; A61F 2/8483; A61F 2/8486; A61F 2220/0016
See application file for complete search history.

(56) References Cited

U.S. PATENT DOCUMENTS

| | | | |
|---|---|---|---|
| 6,099,559 A | 8/2000 | Nolting | |
| 6,241,747 B1 * | 6/2001 | Ruff | ................ A61B 17/06109 411/456 |

(Continued)

FOREIGN PATENT DOCUMENTS

| | | |
|---|---|---|
| JP | 2011509758 A | 3/2011 |
| JP | 2012065825 A | 4/2012 |

(Continued)

OTHER PUBLICATIONS

Alfonso et al., "Implications of the 'Walermelon Seeding' Phenomenon During Coronary Interventions for In-Stent Restenosis," Catheterizalion and Cardiovascular Interventions, 66(4):521-527, Dec. 2005.

(Continued)

*Primary Examiner* — Seema Mathew
(74) *Attorney, Agent, or Firm* — Seager, Tufte & Wickhem, LLP

(57) ABSTRACT

An endoprosthesis has an expanded state and an unexpanded state, the endoprosthesis includes a stent, wherein the stent has a first end, a second end, an inner surface defining a lumen, an outer surface, and a thickness defined between the inner surface and the outer surface; and a stent end covering disposed at one of the first and second ends, the stent end covering including a polymeric coating that includes a base and a plurality of protrusions, the base including a first major surface facing the outer surface of the stent, the base further including a second major surface from which each of the plurality of protrusions extends outwardly, the first major surface opposing the second major surface, wherein the protrusions are arranged in a micropattern. Methods of making and using an endoprosthesis are provided.

16 Claims, 14 Drawing Sheets

Related U.S. Application Data

(60) Provisional application No. 61/798,685, filed on Mar. 15, 2013.

(51) Int. Cl.
*A61F 2/07* (2013.01)
*A61F 2/00* (2006.01)
*A61F 2/04* (2013.01)

(52) U.S. Cl.
CPC .............. *A61F 2/064* (2013.01); *A61F 2/07* (2013.01); *A61F 2002/0081* (2013.01); *A61F 2002/044* (2013.01); *A61F 2002/072* (2013.01); *A61F 2002/075* (2013.01); *A61F 2002/077* (2013.01); *A61F 2002/8483* (2013.01); *A61F 2220/0008* (2013.01); *A61F 2220/0016* (2013.01); *A61F 2250/0063* (2013.01); *Y10T 156/10* (2015.01)

(56) References Cited

U.S. PATENT DOCUMENTS

| | | | |
|---|---|---|---|
| 6,258,099 B1* | 7/2001 | Mareiro | A61F 2/958 604/96.01 |
| 7,744,914 B2 | 6/2010 | Li et al. | |
| 7,763,455 B2* | 7/2010 | Cima | B01L 3/5085 424/449 |
| 7,921,678 B2* | 4/2011 | Norris | A61F 2/07 66/195 |
| 8,323,325 B2* | 12/2012 | Valencia | A61F 2/958 623/1.11 |
| 8,563,117 B2* | 10/2013 | Messersmith | C08J 7/12 428/142 |
| 9,108,880 B2* | 8/2015 | Jin | B81C 1/00206 |
| 10,130,497 B2* | 11/2018 | Krautkremer | A61F 2/04 |
| 10,195,061 B2* | 2/2019 | Weiner | A61F 2/89 |
| 2002/0010489 A1 | 1/2002 | Grayzel et al. | |
| 2002/0082685 A1 | 6/2002 | Sirhan et al. | |
| 2003/0004535 A1 | 1/2003 | Musbach et al. | |
| 2003/0176911 A1 | 9/2003 | Iancea et al. | |
| 2005/0203613 A1* | 9/2005 | Arney | A61F 2/92 623/1.42 |
| 2005/0208100 A1* | 9/2005 | Weber | A61L 27/34 424/426 |
| 2005/0255230 A1 | 11/2005 | Clerc et al. | |
| 2006/0069425 A1 | 3/2006 | Hillis et al. | |
| 2006/0142838 A1* | 6/2006 | Molaei | A61F 2/95 623/1.12 |
| 2007/0038288 A1* | 2/2007 | Lye | A61F 2/07 623/1.16 |
| 2007/0060998 A1 | 3/2007 | Butterwick et al. | |
| 2007/0096048 A1 | 5/2007 | Clerc | |
| 2007/0142907 A1 | 6/2007 | Moaddeb et al. | |
| 2008/0001333 A1* | 1/2008 | Kleine | A61F 2/91 264/564 |
| 2008/0077165 A1 | 3/2008 | Murphy | |
| 2008/0140182 A1 | 6/2008 | Scheller | |
| 2008/0319540 A1 | 12/2008 | Jordan et al. | |
| 2009/0062927 A1 | 3/2009 | Marten et al. | |
| 2009/0088833 A1 | 4/2009 | Soetermans | |
| 2009/0182303 A1 | 7/2009 | Walak et al. | |
| 2009/0187240 A1 | 7/2009 | Clerc et al. | |
| 2010/0076555 A1 | 3/2010 | Marten et al. | |
| 2010/0256064 A1* | 10/2010 | Woolfson | A61B 17/205 514/15.2 |
| 2011/0021965 A1* | 1/2011 | Karp | A61F 2/0077 602/54 |
| 2011/0172760 A1 | 7/2011 | Anderson | |
| 2012/0035715 A1 | 2/2012 | Robida et al. | |
| 2012/0282391 A1 | 11/2012 | Palmaz et al. | |
| 2013/0218262 A1* | 8/2013 | Ishii | A61B 17/0057 623/1.36 |
| 2013/0231753 A1 | 9/2013 | Liddy et al. | |
| 2013/0268063 A1 | 10/2013 | Firstenberg et al. | |
| 2014/0067046 A1* | 3/2014 | Perry | A61F 2/07 623/1.36 |
| 2014/0276203 A1 | 9/2014 | Bertolino et al. | |
| 2014/0276407 A1* | 9/2014 | DeVries | A61B 17/22032 604/103.08 |
| 2014/0277442 A1* | 9/2014 | Seddon | A61F 2/848 623/9 |
| 2014/0277443 A1* | 9/2014 | Fleury | A61L 31/10 623/9 |
| 2014/0277561 A1 | 9/2014 | Jordan | |
| 2014/0364959 A1 | 12/2014 | Attar et al. | |
| 2015/0066136 A1* | 3/2015 | Smith | A61F 2/2409 623/2.11 |
| 2015/0342760 A1* | 12/2015 | Christakis | A61F 2/90 623/1.2 |
| 2016/0120638 A1 | 5/2016 | Michalak | |
| 2016/0128852 A1* | 5/2016 | Leanna | A61F 2/89 623/9 |
| 2016/0158513 A1* | 6/2016 | Ryu | A61M 37/0015 604/103.02 |
| 2017/0014247 A1* | 1/2017 | Ryan | A61F 2/88 |

FOREIGN PATENT DOCUMENTS

| | | |
|---|---|---|
| WO | 9951165 A1 | 10/1999 |
| WO | 2013152338 A1 | 10/2013 |

OTHER PUBLICATIONS

Axisa et al., "Low cost, biocompatible elastic and conformable electronic technologies using MID in stretchable polymer," Proceedings of the 29th Annual International Conference of the IEEE, Lyon, France, 2007:6593-6596, Aug. 24-26, 2007.

Conigliaro et al., "Polyflex stents for malignant oesophageal and oesophagogastric stricture: a prospective, multicentric study," European Journal of Gastroenterology & Hepatology, 19(3):195-203, Mar. 2007.

Conio et al., "A Randomized Prospective Comparison of Self-Expandable Plastic Stents and Partially Covered Self-Expandable Metal Stents in the Palliation of Malignant Esophageal Dysphagia," American Journal of Gastroenterology, 102(12):2667-2677, Dec. 2007.

De La Torre et al., "Chronic Wounds," MedScape Reference—Drugs, Diseases and Procedures, WebMD, LLC., New York, NY, updated Dec. 5, 2011 (available online at http://web.archive.org/web/20111210192504/http://emedicine.medscape.com/a- rticle/1298452-overview, last accessed Jul. 3, 2014), 8 pgs.

Desai et al., "Plastic masters-rigid templates for soft lithography," Lab on a Chip, 9(11):1631-1637, 2009.

Dodou et al., "Mucoadhesive micropatlems for enhanced grip," Proceedings of the 29th Annual International Conference of the IEEE, Lyon, France, 2007:1457-1462, Aug. 24-26, 2007.

Jeong et al., "Nanohairs and nanotubes: Efficient structural elements for gecko-inspired artificial dry adhesives," Nano Today, 4(4):335-346, Aug. 2009.

Kroetch, "NanoFab's PDMS Microfluidic Device Fabrication Manual," University of Alberta, Alberta, Canada; 8 pgs, Sep. 2004 (available online at http://www.nanofab.ualbelta.ca/wp-content/uploads/2009/03/boxedpdms.pdf, last accessed Mar. 10, 2013).

Kwon et al., "Friction enhancement via micro-patterned wet elastomer adhesives on small intestinal surfaces," Biomedical Materials, 1(4):216-220, Dec. 2006.

Lotters et al., "The mechanical properties of the rubber elastic polymer polydimethylsiloxane for sensor applications," Journal of Micromechanics and Micro engineering, 7(3):145-147, 1997.

Mahdavi et al., "A biodegradable and biocompatible gecko-inspired tissue adhesive," Proceedings of the National Academy of Sciencess, U.S.A., 105(7):2307-2312, Feb. 19, 2008.

Majidi, "Enhanced Friction and Adhesion with Biologically Inspired Fiber Arrays," University of California, Berkeley, Ph.D. thesis, 143 pgs, May 15, 2007.

(56) References Cited

OTHER PUBLICATIONS

Schembre, "Advances in esophageal stenting: the evolution of fully covered stents for malignant and benign disease," Advanced Therapy, 27(7):413-425, Jul. 2010.

Sharma et al., "Role of esophageal stents in benign and malignant diseases," American Journal of Gastroenterology, 105(2):258-273, Dec. 2009.

Shim, "Esophageal stenting in unusual situations," Endoscopy, 35:14-18, 2003.

Throm Quinlan et al., "Combining dynamic stretch and tunable stiffness to probe cell mechanobiology in vitro," PLoS One, 6(8):e23272, Aug. 2011.

Tooley et al., "Thermal fracture of oxidized polydimethylsiloxane during soft lithography of nanopost arrays," Journal of Micromechanics and Microengineering, 21 :054013, 1-9, Apr. 2011.

Van Boeckel et al., "A new partially covered metal stent for palliation of malignant dysphagia: a prospective follow-up study," Gastrointestinal Endoscopy, 72(6):1269-1273, Dec. 2010.

Yoon et al., "Passive control of cell locomotion using micropatterns: the effect of micropattern geometry on the migratory behavior of adherent cells," Lab Chip, 12, 2391-2402 (12 pages), 2012.

Yoon et al., "Passive control of cell locomotion using micropatterns: the effect of micropattern geometry on the migratory behavior of adherent cells," Lab on a Chip, 12(13): Electronic Supplementary Material (ESI) pp. S1-S11, 2012.

\* cited by examiner

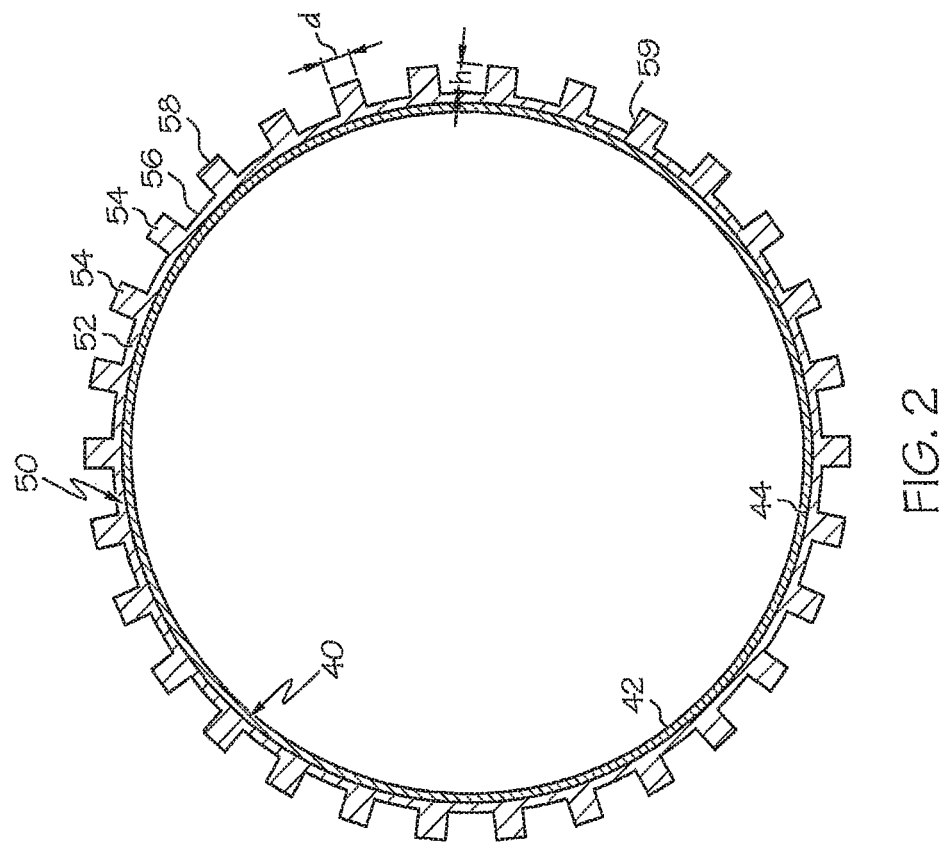
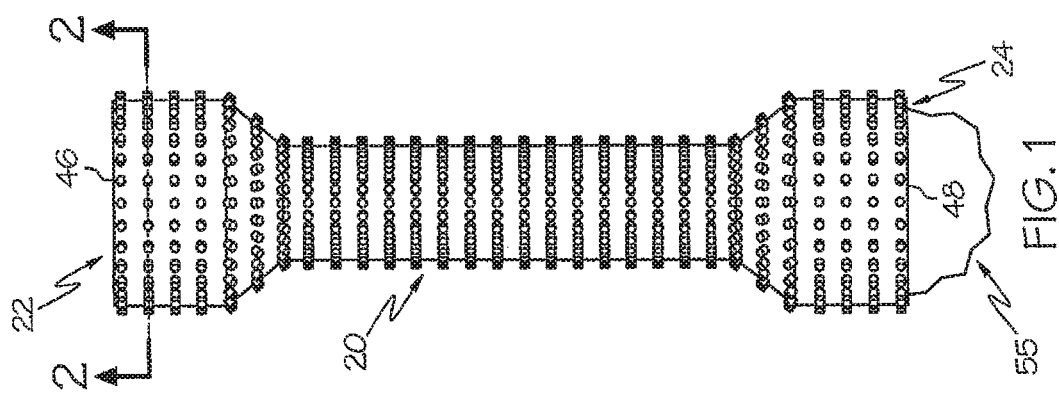

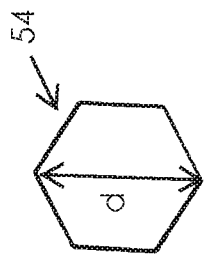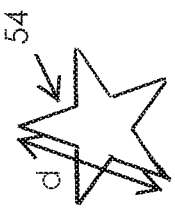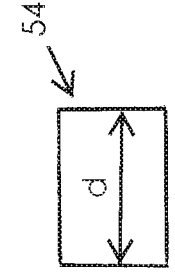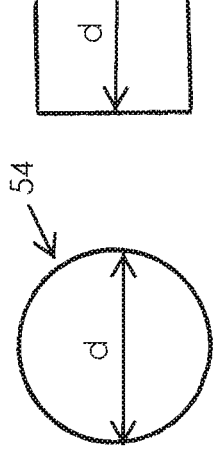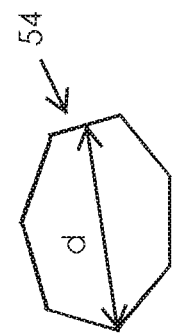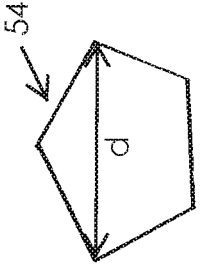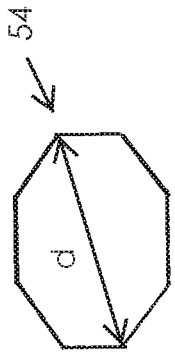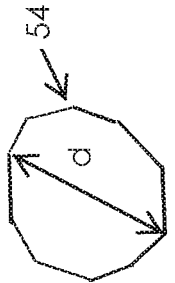

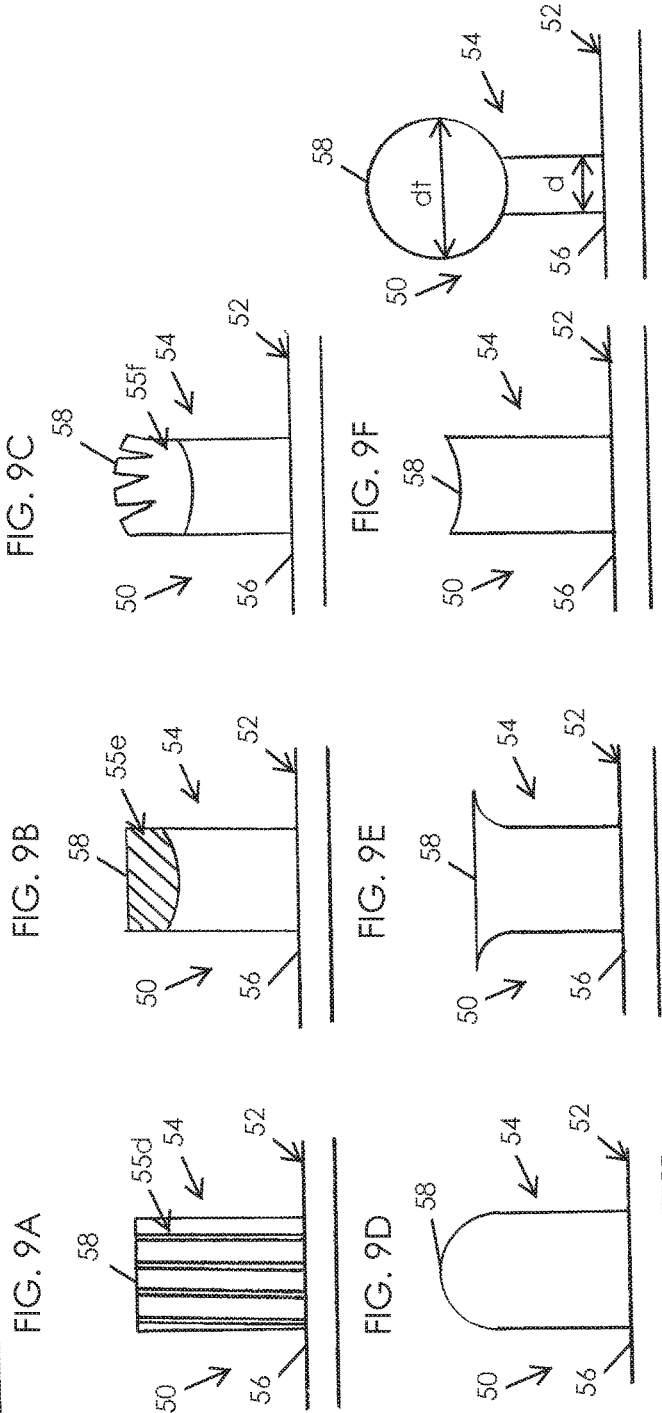

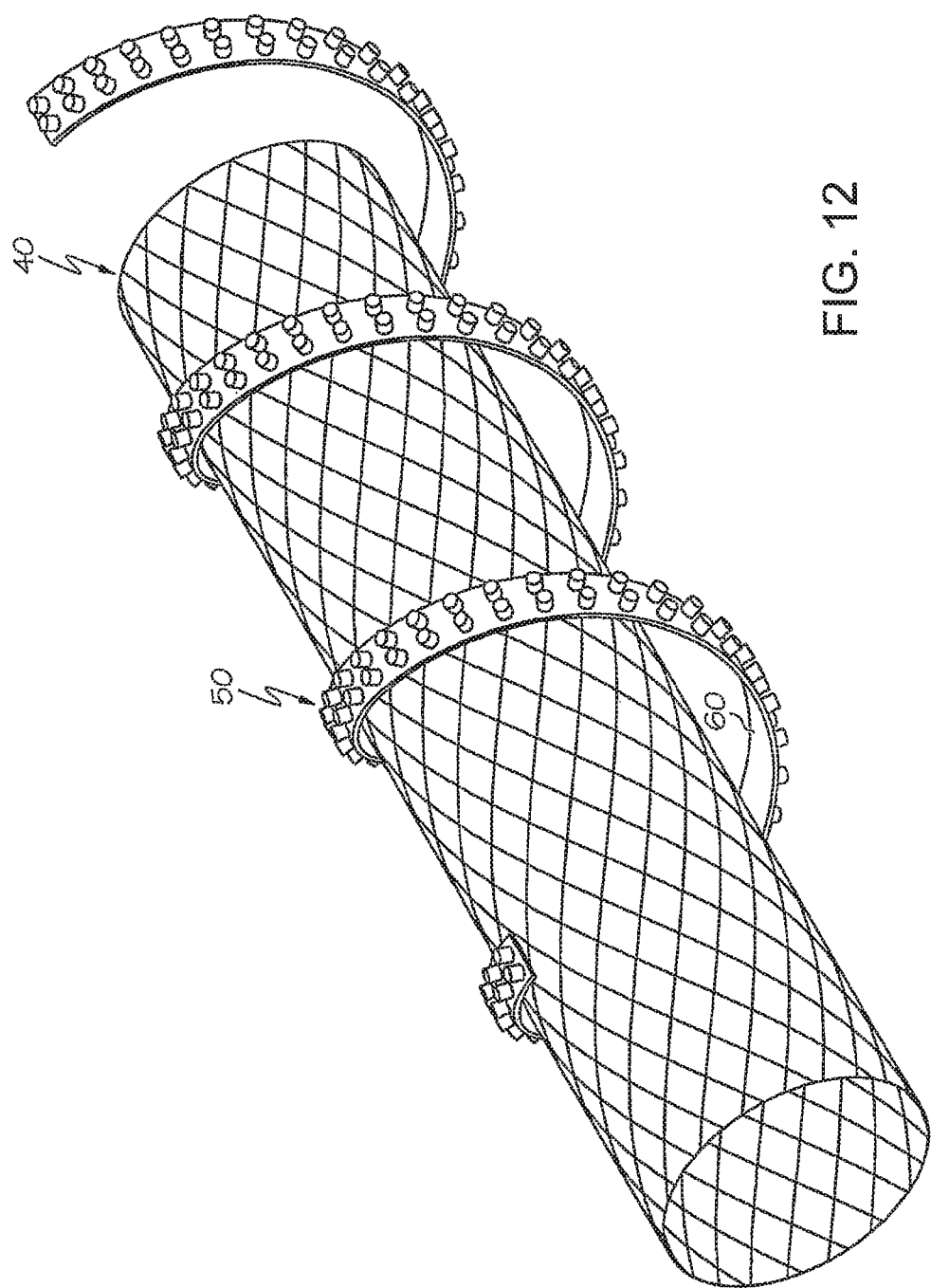

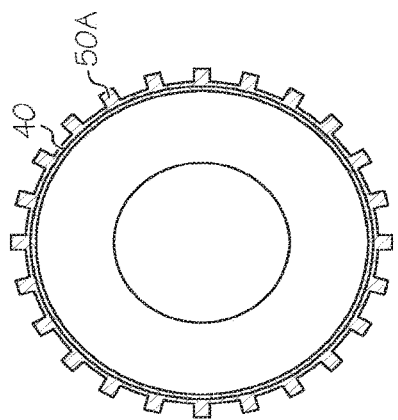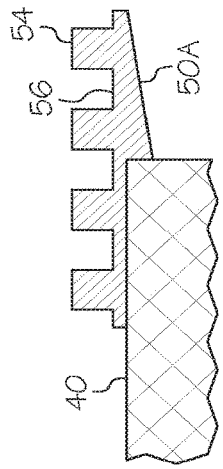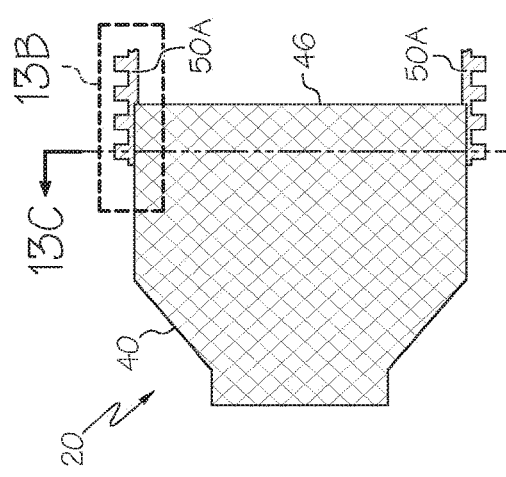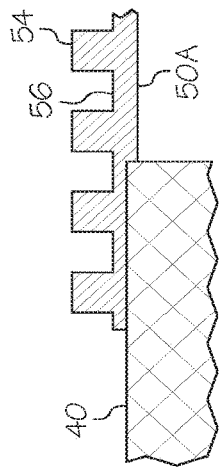

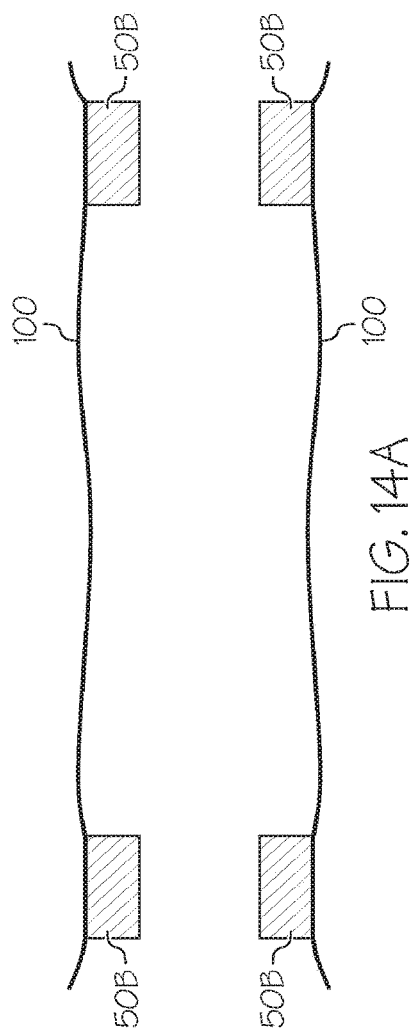
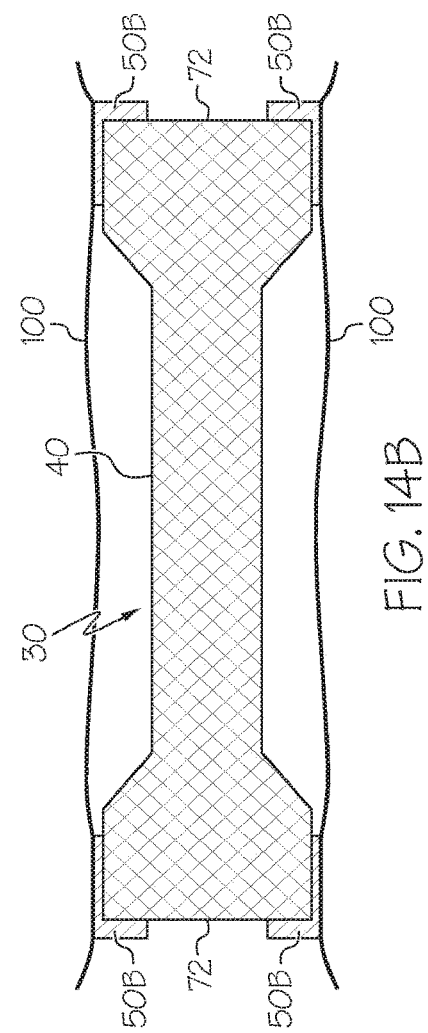

ANTI-MIGRATION MICROPATTERNED STENT COATING

CROSS REFERENCE TO RELATED APPLICATIONS

This application is a continuation of U.S. application Ser. No. 14/210,979, filed Mar. 14, 2014, which claims the benefit of provisional U.S. Patent Application No. 61/798,685, filed on Mar. 15, 2013), which is hereby incorporated by reference in its entirety.

The following patent applications are incorporated herein by reference, each in its entirety:

U.S. Patent Application No. 61/798,897 (Seddon et al.), entitled ANTI-MIGRATORY STENT COATING, filed on Mar. 15, 2013;

U.S. Patent Application No. 61/798,794 (Clerc), entitled DELIVERY DEVICE FOR PARTIALLY UNCONSTRAINED ENDOPROSTHESIS, filed on Mar. 15, 2013;

U.S. Patent Application No. 61/799,312 (Fleury et al.), entitled SUPERHYDROPHOBIC COATING FOR AIRWAY MUCUS PLUGGING PREVENTION, filed on Mar. 15, 2013;

U.S. Patent Application No. 61/798,545 (Leanna et al.), entitled MEDICAL DEVICES HAVING MICROPATTERN, filed on Mar. 15, 2013; and U.S. Patent Application No. 61/798,991 (Bertolino et al.), entitled BIOPSY TOOL HAVING MICROPATTERN, filed on Mar. 15, 2013.

BACKGROUND OF THE INVENTION

A stent is a medical device introduced into a body lumen and is well known in the art. A stent may be delivered in an unexpanded state to a desired location in a bodily lumen and then expanded by an internal radial force. Stents, grafts, stent-grafts, vena cava filters, expandable frameworks, and similar implantable medical devices, collectively referred to hereinafter as stents, have included radially expandable endoprostheses, which have been used as intravascular implants capable of being implanted transluminally.

Esophageal stents have been used to treat patients suffering from a range of malignant and non-malignant diseases. Most commonly, esophageal stents have been associated with the treatment of esophageal cancers. Esophageal stents have also been used to reduce symptoms resulting from non-esophageal tumors that grow to obstruct the esophagus and to treat benign esophageal disorders, including but not limited to refractory strictures, fistulas and perforations. In each of these cases, esophageal stents may provide mechanical support to the esophageal wall and may maintain luminal patency. Because of the structure of the esophagus and conditions such as peristalsis, esophageal stents have been prone to stent migration.

One way to reduce the risk of stent migration has been to expose bare metal portions of the stent to esophageal tissue. The open, braided structure of the stent may provide a scaffold that promotes tissue ingrowth into the stent. This tissue ingrowth may aid anchoring the stent in place and may reduce the risk of migration. In some cases, however, tissue ingrowth has been known to lead to reocclusion of the esophagus. In addition, esophageal stents anchored by tissue ingrowth cannot be moved or removed without an invasive procedure. To reduce tissue ingrowth, stents have been covered with a coating (e.g., made of a polymer, etc.) to create a physical barrier between the lumen and the esophageal wall. However, in some circumstance, such stents can have an unacceptable occurrence of migration, as compared to bare metal counterparts.

Another way to reduce the risk of stent migration has been to use a flared stent in the esophagus. However, stents having flares can have an unacceptable occurrence of migration.

Granulation tissue caused by stents (e.g., endoprostheses) may occur due to repeated trauma to a wall of a body lumen (e.g., a gastrointestinal wall, a tracheal wall, etc.) and due to subsequent lack of proper wound healing. In some circumstances, granulation tissue, especially in excess, can not only impede flow of solids and/or fluids (e.g., liquid and vapor) through the body lumen (e.g., mucous clearance, air movement, fluid movement, etc.) due to the reduction in the body lumen cross-sectional area (e.g., reduction in radius, etc.), but also because the granulation tissue has a tendency to latch onto the endoprosthesis, which may increase the difficulty of removing the endoprosthesis when necessary. Physician preference has trended toward endoprostheses that are removable and atraumatic.

Improved stents with, for example, improved resistance to migration, improved stent adhesion to the esophageal wall, and/or improved removability are desired. Previous tracheal stents, such as those discussed in US Patent Publication Nos. 2006/0069425 and 2009/0062927, which are incorporated by reference herein in their entireties, have incorporated bumps or other surface features into the stent itself. Another tracheal stent described in co-owned US Patent Publication No. 2012/0035715, which is incorporated by reference herein in its entirety, also provides a plurality of surface protrusions on the outer surface of the stent.

Without limiting the scope of the present disclosure, a brief summary of some of the claimed embodiments is set forth below. Additional details of the summarized embodiments of the present disclosure and/or additional embodiments of the present disclosure may be found in the Detailed Description of the Invention below. A brief abstract of the technical disclosure in the specification is also provided. The abstract is not intended to be used for interpreting the scope of the claims.

BRIEF SUMMARY OF THE INVENTION

The present disclosure provides an endoprosthesis where a preferably polymeric coating has a number of surface features such as protrusions that are arranged in a micropattern.

In at least one embodiment, an endoprosthesis, having an expanded state and a contracted state, includes a stent with a polymeric coating adhered to an outer surface of the stent. The stent has an inner surface defining a lumen. In at least one embodiment, the stent is a flared stent. The polymeric coating includes a base and a plurality of protrusions (e.g., micropillars, etc.) extending outwardly from the base. In at least one embodiment, the protrusions are arranged in a micropattern. When the endoprosthesis is expanded to the expanded state in a lumen defined by a vessel wall, the micropillars apply a force that creates an interlock between the vessel wall and the endoprosthesis.

The micropattern is specifically designed for a particular tissue in order to effectively interlock the stent with the tissue. In at least one embodiment, the micropattern is present along at least a portion of the endoprosthesis. In at least one embodiment, the protrusions of the micropattern can be uniform or the micropattern can be formed of protrusions having a first configuration and protrusions having at least a second configuration.

The protrusions may be micropillars and may be selected from a group including cylinders, rectangular prisms, and similar structures. In at least one embodiment, the protrusions of the micropattern are cylindrical micropillars, each cylindrical micropillar having a diameter and a height, wherein the diameter of each cylindrical micropillar is equal to its height. In at least one embodiment, the cylindrical micropillar has a lateral surface, wherein the lateral surface of the cylindrical micropillar is separated from the lateral surfaces of an adjacent micropillar by a distance greater than the diameter of the cylindrical micropillar. In at least one embodiment, the micropattern is a grid pattern.

In at least one embodiment, each protrusion of the micropattern has a first dimension and a second dimension, wherein the first dimension is between about 1 μm and 100 μm, wherein the second dimension is between about 1 μm and 100 μm, and wherein each protrusion is spaced apart from an adjacent protrusion by a distance, wherein a ratio between the distance and the first dimension is between about 2.1 and 2.4. In at least one embodiment, each protrusion has a ratio between the first dimension and the second dimension that is between about 1 and 1.3.

In at least one embodiment, the endoprosthesis is retrievable by, for example, a retrieval loop at a distal end of the stent.

In at least one embodiment, an endoprosthesis may include one or more endoprosthesis ends having a covering attached thereto having a micropatterned surface that may extend circumferentially around at least a portion of an endoprosthesis end and may extend longitudinally beyond an endoprosthesis end in a cantilever configuration. In one or more embodiments, the cantilevered portion of the endoprosthesis end covering may extend beyond the stent end by a distance that is at least two times (e.g., at least three times, at least four times, etc.) the thickness of the cantilevered portion or the thickness may be less than two times (e.g., less than one times, less than one-half of) the thickness of the cantilever portion. In at least one embodiment, an endoprosthesis end covering having a micropatterned surface may be deployed in a body lumen separately from an endoprosthesis, wherein the endoprosthesis end covering may be deployed in a body lumen followed by deployment of an endoprosthesis wherein an endoprosthesis end is disposed within at least a portion of the endoprosthesis end covering (e.g., the endoprosthesis end covering may be biased between the endoprosthesis end and the wall of the body lumen).

Several methods of manufacturing an embodiment of the endoprosthesis are provided. One method of manufacturing includes forming a polymeric coating, wherein the polymeric coating includes a base and a plurality of protrusions extending outwardly from the base in a micropattern; providing a stent having an inner surface defining a lumen and an outer surface; and adhering the base of the polymeric coating to the outer surface of the stent. The polymeric coating can be formed using a mold having an inverse of the micropattern and injecting a polymeric material into the mold and, in some cases applying temperature or pressure to the mold, before the polymeric material cures; using soft lithography techniques, or by etching the polymeric coating from a layer of the polymeric material. In at least one embodiment, an adhesive layer is applied to at least one of a surface of the base and the outer surface of the stent. In at least one embodiment, the polymeric coating is formed as a tubular structure. In one or more embodiments, the polymeric coating is formed in a strip, which is wrapped (e.g., helically wrapped, circumferentially wrapped, randomly wrapped, etc.) about the outer surface of the stent.

In at least one embodiment, an endoprosthesis may have an expanded state and an unexpanded state, the endoprosthesis including a stent, wherein the stent has a first end, a second end, an inner surface extending from the first end to the second end and defining a lumen, an outer surface extending from the first end to the second end, and a thickness defined between the inner surface and the outer surface; and a stent end covering disposed at one of the first and second ends, the stent end covering including a polymeric coating comprising a base and a plurality of protrusions, the base comprising a first major surface facing the outer surface of the stent, the base further comprising a second major surface from which each of the plurality of protrusions extends outwardly, the first major surface opposing the second major surface, wherein the protrusions are arranged in a micropattern.

In one or more embodiments, the stent end covering is adhered to the outer surface of the stent, the inner surface of the stent, or both. In one or more embodiments, the stent end covering extends circumferentially and entirely around one of the first and second ends of the stent. In at least one embodiment, stent end covering extends circumferentially and partially around one of the first and second ends. In one or more embodiments, the stent end covering extends longitudinally from a location between the first and second ends to a location that is not between the first and second ends. In at least one embodiment, at least a first portion of the stent end covering has a radial thickness greater than the thickness of the stent at the stent end that is nearest to the stent end covering. In some embodiments, at least a second portion of the stent end covering has a radial thickness less than the radial thickness of the first portion of the stent end covering. In at least one embodiment, an endoprosthesis may include a first stent end covering and a second stent end covering, wherein one of the first and second stent end coverings is disposed at the first end of the stent and one of the first and second stent end coverings is disposed at the second end of the stent.

In one or more embodiments, a method of manufacturing an endoprosthesis includes forming a stent end covering that includes a polymeric coating, wherein the polymeric coating includes a base and a plurality of protrusions, the base including a first major surface facing the outer surface of the stent, the base further including a second major surface from which each of the plurality of protrusions extends outwardly, the first major surface opposing the second major surface, wherein the protrusions are arranged in a micropattern; the method also including providing a stent having a first end, a second end, an inner surface extending from the first end to the second end and defining a lumen, an outer surface extending from the first end to the second end, and a thickness defined between the inner surface and the outer surface; the method also including contacting the stent end covering with one of the first and second ends of the stent.

In one or more embodiments, the contacting further includes contacting the stent end covering with the outer surface of the stent. In one or more embodiments, the contacting further includes contacting the stent end covering with the inner surface of the stent. In at least one embodiment, the contacting includes disposing the stent end covering circumferentially and entirely around one of the first and second ends. In one or more embodiments, the contacting includes disposing the stent end covering wherein the stent end covering extends longitudinally from a location between the first and second ends of the stent to a location that is not between the first and second ends of the stent. In some embodiments, the method further includes disposing the stent end covering within a body lumen, wherein disposing the stent end covering within the body lumen occurs before contacting the stent end covering with one of the first and second ends of the stent. In one or more embodiments, the contacting includes deploying the stent within the body lumen, wherein the stent end covering is disposed between a lumen wall of the body lumen and one of the first and second ends of the deployed stent. In some embodiments, forming the stent end covering including the polymeric coating includes using a mold having an inverse of the micropattern and injecting a polymeric material into the mold. In at least one embodiment, the contacting includes applying an adhesive to at least one of a surface of the base and the outer surface of the stent.

In one or more embodiments of the present disclosure, a method of using an endoprosthesis includes providing a stent end covering that includes a polymeric coating, wherein the polymeric coating includes a base and a plurality of protrusions, the base including a first major surface facing the outer surface of the stent, the base further including a second major surface from which each of the plurality of protrusions extends outwardly, the first major surface opposing the second major surface, wherein the protrusions are arranged in a micropattern; the method further including providing a stent having a first end, a second end, an inner surface extending from the first end to the second end and defining a lumen, an outer surface extending from the first end to the second end, and a thickness defined between the inner surface and the outer surface; disposing the stent end covering within a lumen; and after disposing the stent end covering within a lumen, contacting the stent end covering with one of the first and second ends of the stent. In some embodiments, the contacting includes deploying a stent within the lumen.

BRIEF DESCRIPTION OF THE SEVERAL VIEWS OF THE DRAWING(S)

FIG. 1 shows a plan view of the endoprosthesis of the present disclosure.

FIG. 2 shows a cross-section of the endoprosthesis shown in FIG. 1.

FIGS. 8A-8J show cross-sections of the micropillars of the polymeric coating shown in FIGS. 3-6.

FIGS. 9A-9J show plan views of embodiments of the polymeric coating shown in FIG. 3.

FIG. 12 is a view of the stent and polymeric coating during one method of manufacturing the endoprosthesis.

FIGS. 13A-13D are schematics showing at least one embodiment of a stent end covering.

FIGS. 14A-14B are schematics of at least one embodiment of a stent end covering that may be implanted before a corresponding stent.

DETAILED DESCRIPTION OF THE INVENTION

Figure 3:
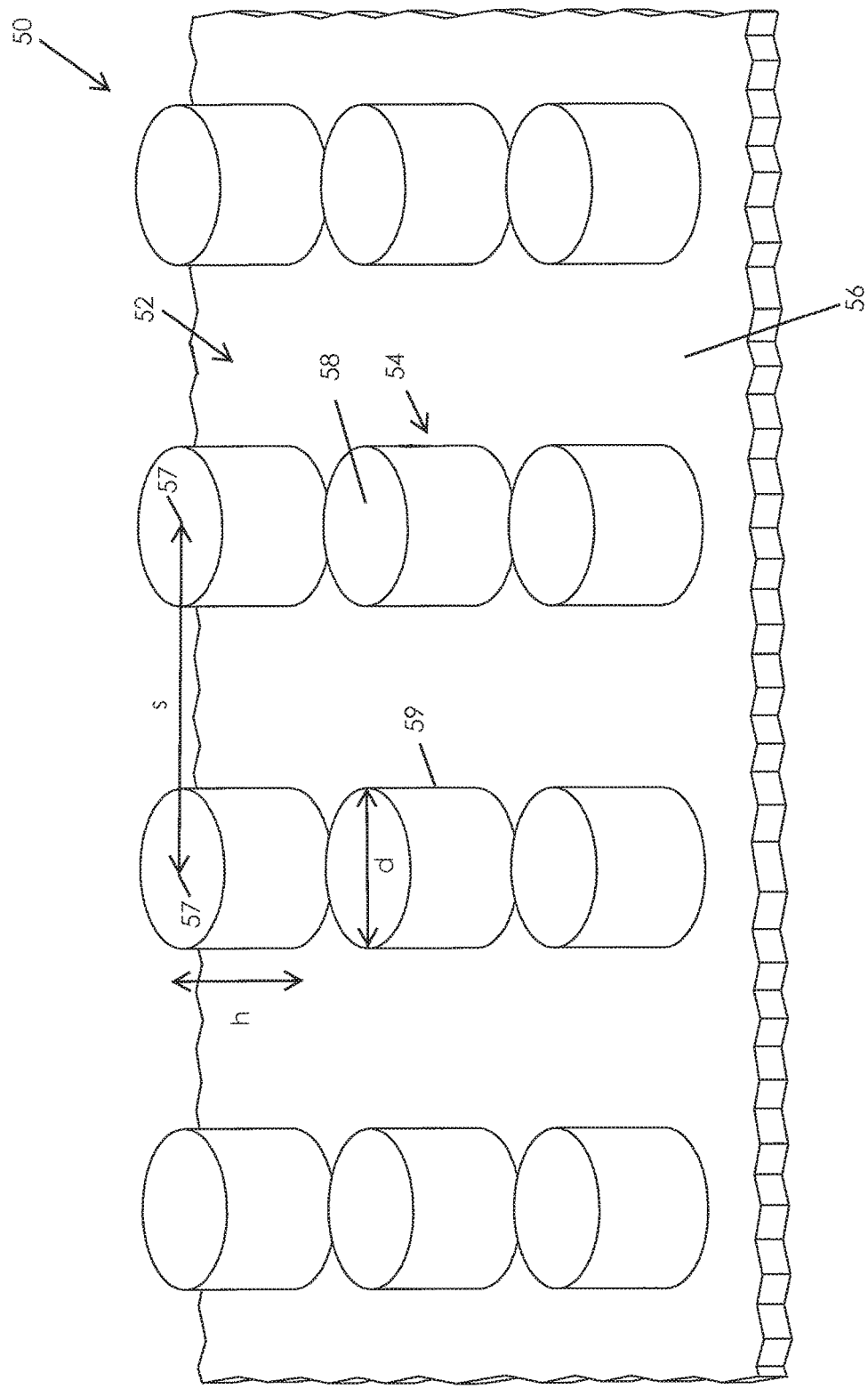
FIG. 3 is an enlarged view of the polymeric coating of the endoprosthesis shown in FIG. 1.
Figure 4:
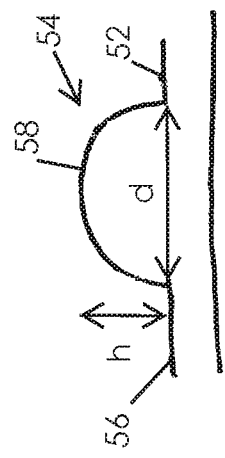
FIG. 4 shows a cross-section of a portion of the polymeric coating shown in FIG. 3.
Figure 5:
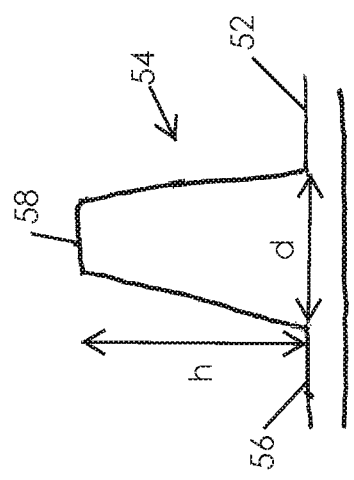
FIGS. 5-7 show cross-sections of portions of embodiments of the polymeric coating.

While the subject matter of the present disclosure may be embodied in many different forms, there are described in detail herein specific preferred embodiments of the present disclosure. This description is an exemplification of the principles of the present disclosure and is not intended to limit the present disclosure to the particular embodiments illustrated.

For the purposes of this disclosure, like reference numerals in the figures shall refer to like features unless otherwise indicated. A reference numeral that includes a letter (e.g., 50A, 50B, etc.) shall be considered to be a like reference numeral. For example, polymer coating 50, stent end covering 50A, and stent end covering 50B all have like reference numerals and refer to like features unless otherwise indicated.

The present disclosure relates to micropatterned polymeric coatings for use on medical devices. In some embodiments, the micropatterned polymeric coatings are utilized with implantable medical devices, such as stents, to reduce or prevent stent migration, particularly for stents used in the gastroesophageal system, including, but not limited to, esophageal, biliary, and colonic stents. The stents described in this application may also be used in the trachea, the cardiovascular system, and elsewhere in the body (e.g., any body lumen). The present disclosure also relates to micropatterned polymeric coatings to be applied to, for example, stent ends, which may reduce trauma, promote wound healing, and reduce or avoid granulation tissue buildup.

FIGS. 1 and 2 show an esophageal endoprosthesis 20 of the present disclosure with a proximal end 22 and a distal end 24. The endoprosthesis 20 includes an expandable stent 40 and a polymeric coating 50. Expandable stent 40 can be self-expanding, balloon expandable, or hybrid expandable. Embodiments of the expandable stent 40 contemplate stents having a constant diameter, tapers, flares and/or other changes in diameter in the body and/or at an end. The expandable stent 40 has an inner surface 42, an outer surface 44, a first end 46 and a second end 48, and the polymeric coating 50 is disposed about at least a portion of the outer surface 44. In at least one embodiment, the polymeric coating 50 substantially covers the entire outer surface 44 of the expandable stent 40. In other embodiments, the polymeric coating 50 covers a portion of the outer surface 44 of the expandable stent 40. As shown in FIG. 2, the polymeric coating 50 can be directly connected to the outer surface 44 of the expandable stent 40. In one or more embodiments, the polymeric coating 50 can be connected to the outer surface 44 of the expandable stent 40 using an adhesive or other means of attaching the coating to the device. In at least one embodiment, the polymeric coating at least partially covers the inner surface 42 also. In at least one embodiment, partial coverage can include partial coverage of the perimeter and/or the length. In some embodiments, the polymer coating 50 and the stent 40 can be integral (e.g., collectively formed as an integral construction). For example, in one or more embodiments in which at least a portion a stent 40 is made of a material (e.g., silicone, silicone coating, biocompatible polymer or metal, etc.) appropriate for micropatterning, then the micropattern may be directly incorporated into the structure of the stent 40 (e.g., the stent 40 and polymer coating 50 having a micropattern can be integrally formed).

In at least one embodiment, shown in FIGS. 2 and 3, the polymeric coating 50 includes a base 52 and a plurality of protrusions, such as micropillars 54, extending outwardly from the base 52. In at least one embodiment, the micropillars are seamlessly incorporated into the base of the coating. In at least one embodiment, the base 52 is coterminous with the expandable stent 40. What is meant by "coterminous" is that the base 52 of the polymer coating 50 and the expandable stent 40 have the same boundaries, cover the same area, and are the same in extent. In other words, the expandable stent 40 and the base 52 each have first and second ends, and the expandable stent 40 and the base 52 extend between their first and second ends. The first end of the expandable stent 40 is the same as first end of the base 52, and the second end of the expandable stent 40 is the same as the second end of the base 52. Since the expandable stent 40 and the base 52 extend between their first and second ends, the expandable stent 40 and the base 52 have the same boundaries, cover the same area, and are the same in extent. Thus, the base 52 and the expandable stent 40 are coterminous. The expandable stent 40 and the base 52 therefore are coterminous in at least one embodiment. Also, base 52 is tubular in at least one embodiment.

Figure 7:
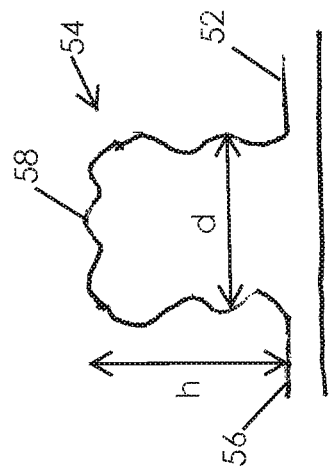
Figure 6:
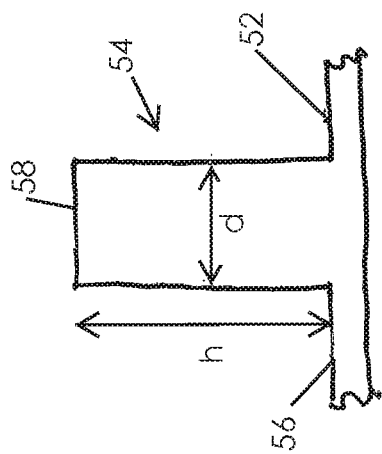

In some embodiments as shown in FIGS. 3-7, the micropillars are cylinders (FIG. 3), prisms with a rectangular or polygonal base (FIG. 4), pyramids (FIG. 5), bumps (FIG. 6), or has a non-traditional shape with a plurality of bumps and ridges on multiple surfaces that do not define a cross-section that is circular, square, polygonal, etc. (FIG. 7). Each micropillar can have a circular cross-section (FIG. 8A), square cross-section (FIG. 8B), rectangular cross-section (FIG. 8C), star-shaped cross-section (FIG. 8D), hexagonal cross-section (FIG. 8E), pentagonal cross-section (FIG. 8F), heptagonal (FIG. 8G), octagonal cross-section (FIG. 8H), nonagonal cross-section (FIG. 8I), decagonal cross-section (FIG. 8J), other polygonal cross-sections, or non-traditional shaped cross-sections. Each cross-section has a first dimension h that is the greatest distance between the outer surface of the base and the end of the pillar and a second dimension d that is the greatest distance between two opposite sides (e.g., of the pillar). For example, for the circular cross-section the second dimension d is the diameter, for the square d is between two sides, for the rectangle, the major dimension is between the two shorter sides, for the star, the major dimension is between two points, for the hexagon the major dimension is between two opposite points. In some embodiments, the second dimension d is between midpoints of two opposite sides. In at least one embodiment, a cross section of the micropillar taken in the radial direction has at least four sides. Embodiments of the present disclosure contemplate polygonal cross-sections having all sides of equal length, combinations of sides of equal length and unequal length, or all sides of unequal length. Embodiments of the present disclosure contemplate multiple pillars of multiple cross-sectional shapes including traditional shapes (e.g. circles, squares, rectangles, hexagons, polygons, etc.) and non-traditional shapes having a perimeter where at least a portion of the perimeter is curvilinear. In at least one embodiment, the micropillars are solid structures, but in other embodiments they can be hollow structures. In at least one embodiment, each micropillar has a constant cross-section, but in other embodiments the micropillars have variable cross-sections. In at least one embodiment, the plurality of micropillars 54 can be arranged in one or more particular micropatterns. Although not wishing to be bound by theory, the micropattern may affect the strength of the frictional engagement or interlock between the endoprosthesis and the vessel wall. Likewise, the micropattern is dependent upon the desired frictional engagement or interlock between the micropillars of the endoprosthesis and the tissue. For this reason, in at least one embodiment, a particular microstructure can be selected that has a micropattern geometry and dimensions suitable for a particular application (e.g., implantation site, biological tissue, desired tissue engagement properties, etc.).

In at least one embodiment, the micropillars in the micropattern all have the same shape, and in other embodiments, the micropillars vary in shape along the polymeric coating. Thus, in at least one embodiment, the micropattern can include portions where the micropillars have a first configuration and portions where the micropillars have a second configuration. Moreover, embodiments include the polymeric coating having only one micropattern or the polymeric coating having multiple micropatterns. Thus, the polymeric coating can be tailored to specific structural characteristics of the body lumen (e.g., a vessel, etc.) and a desired frictional engagement or interlock can be achieved, while using a single stent.

In at least one embodiment, the dimension d is between 1 µm and 100 µm. In at least one embodiment, the dimension d is between about 14 µm and 18 µm. In at least one embodiment, the dimension d is at least equal to the dimension h. In at least one embodiment, a ratio of h to d is between about 1 and 1.3. In at least one embodiment, two adjacent micropillars are spaced apart by a distance s (shown in FIG. 3). In at least one embodiment, the ratio of the spacing s to the dimension d is between about 2.1 and 2.4.

In some embodiments, the ends of the protrusions, such as micropillars 54, that are furthest away from the outer surface of the base can be shaped to improve tissue attachment. In one or more embodiments, the ends can be tapered, pointed, rounded, concave, convex, jagged, or frayed. The ends of each protrusion (micropillar 54) can include a plurality of pillars on an even smaller scale than micropillars 54.

In at least one embodiment, the protrusions such as micropillars 54 can also include features such as smooth surfaces, rough surfaces 55a (FIG. 9A), a plurality of bumps 55b extending outwardly from a surface of the micropillar (FIG. 9B), a plurality of indentations 55c extending inwardly from a surface of the micropillar (FIG. 9C), a plurality of ridges 55d on a surface of the micropillar (FIG. 9D), a tip 55e at or near the end of the protrusion that either softer or more rigid than the remainder of the protrusion (FIG. 9E), a frayed tip 55f (FIG. 9F), and other features that may impart desirable gripping, stiffness, or flexibility characteristics for the endoprosthesis, and any combination of features thereof. In at least one embodiment, the tip 55e can include a different material than the remainder of the protrusion.

FIG. 3 shows an enlarged view of the polymeric coating 50. In at least one embodiment, the micropillars are cylinders that each have a diameter d and a height, h measured from an outer surface of the base 56 to a top surface of the cylinder 58. In at least one embodiment, the diameter d is between 1 μm and 100 μm. In at least one embodiment, the diameter d is between about 14 μm and 18 μm. In at least one embodiment, the diameter d of the micropillar is at least equal to its height h. In at least one embodiment, a ratio of height h of the micropillar 54 to diameter d of the micropillar is between about 1 and 1.3. In at least one embodiment, the micropillars each have a lateral surface 59. In at least one embodiment, two adjacent micropillars are spaced apart. The micropillars should be spaced apart enough so that the tissue of the bodily vessel can fill the negative space (e.g., void space) between the pillars. If the spacing is too small, the tissue may not be able to actually interlock. In at least one embodiment, the spacing between the micropillars is dependent upon (e.g., may be selected based upon) the particular type of tissue of the bodily vessel. In at least one embodiment, the spacing s measured between the centers 57 of one micropillar and an adjacent micropillar is greater than the diameter d of the one micropillar. In at least one embodiment, the ratio of the spacing s to the diameter d is between about 2.1 and 2.4.

Figure 10A:
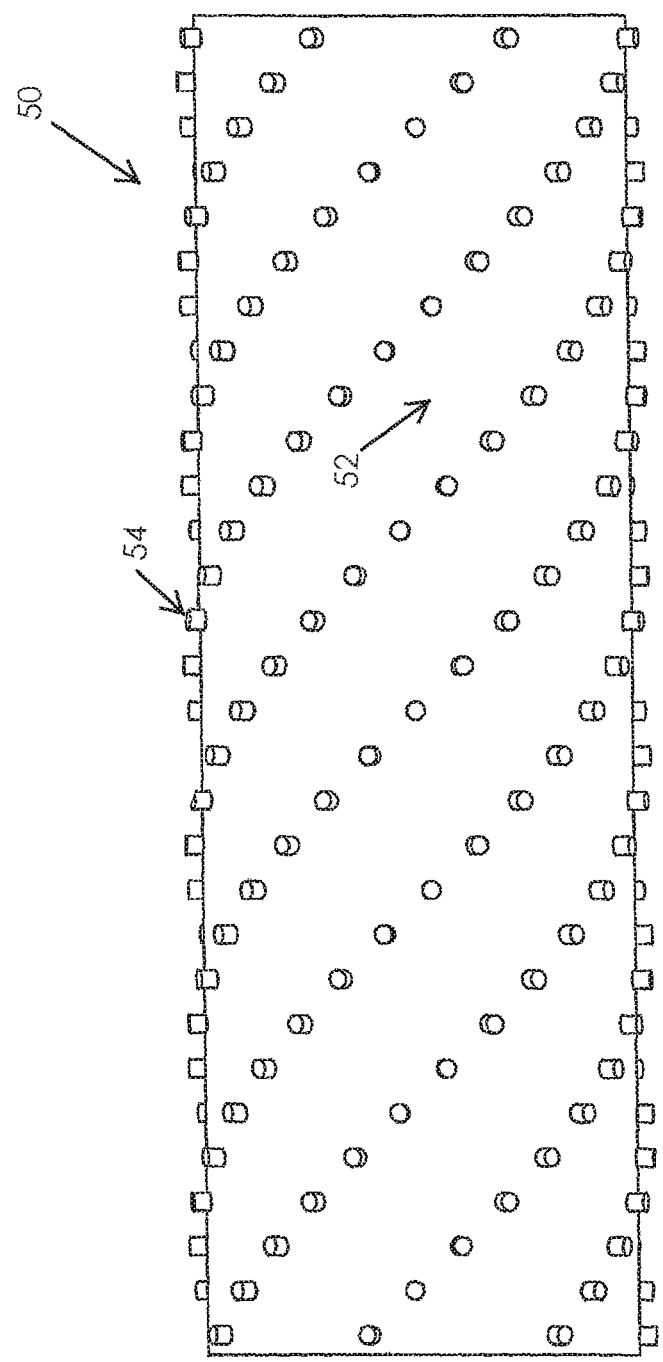
FIG. 10A shows an embodiment of the polymeric coating of the present disclosure.
Figure 10B:
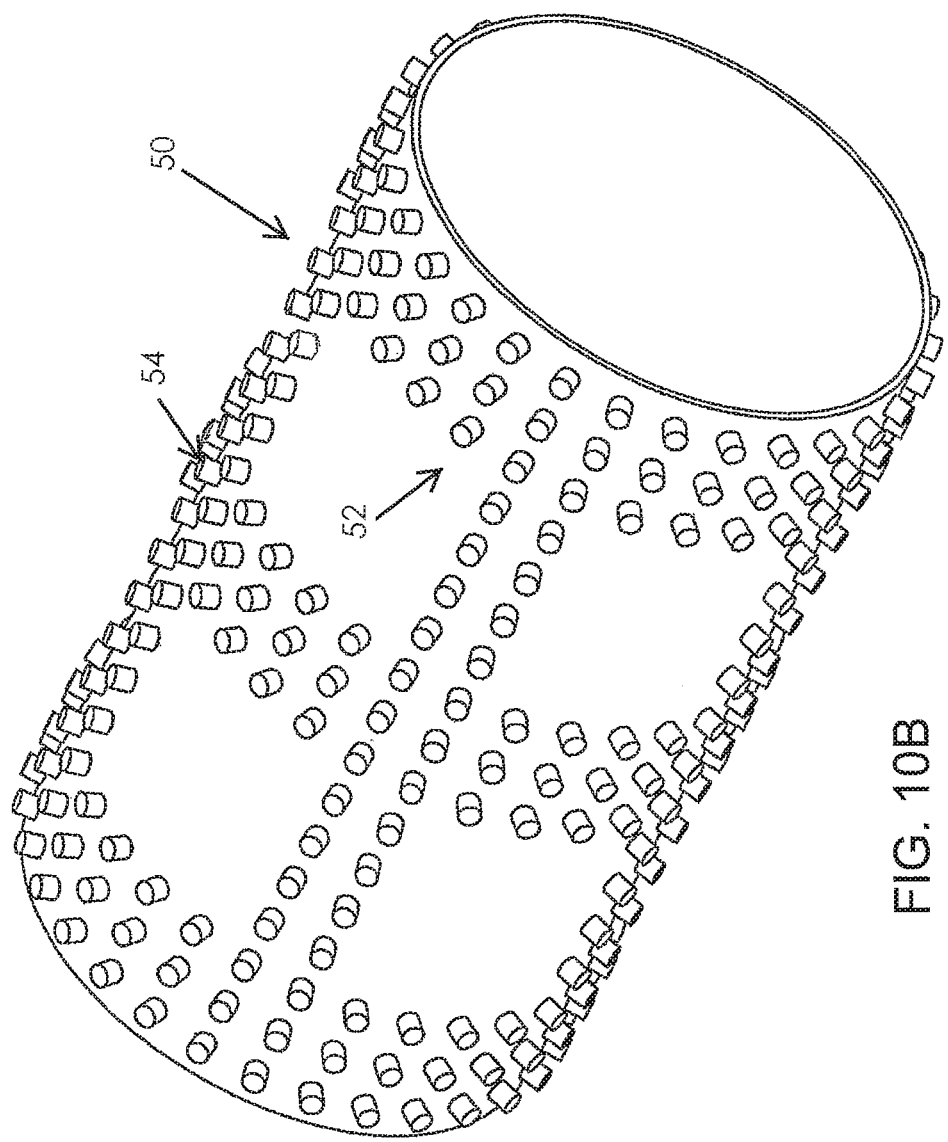
FIG. 10B shows an embodiment of the polymeric coating of the present disclosure.

In at least one embodiment, the micropillars are spaced apart equidistantly in the micropattern. In at least one embodiment, the micropattern of micropillars is a rectangular array. In at least one embodiment, the micropattern is a grid pattern. In other words, in the micropattern, the micropillars are arranged in rows and columns in the micropattern, wherein the rows and columns may or may not be perpendicular. In one or more embodiments, each micropillar has a longitudinal axis and the micropillars are axially aligned in at least one of the axial direction (e.g., arranged in a row parallel to a longitudinal axis of a stent) and the circumferential direction of the endoprosthesis (e.g., arranged in a row extending circumferentially around a longitudinal axis of a stent). In at least one embodiment, the micropattern of micropillars includes any or all of the features described in this paragraph. In some embodiments, like the embodiments shown in 10A and 10B, the micropattern may cover only a portion of the base 52 rather than the entire base 52. The micropattern of micropillars may be helically disposed on the base 52, as shown in FIG. 10A. In one or more embodiments, as shown in FIG. 10B, a first micropattern may be disposed longitudinally along the base 52 and a second micropattern is disposed circumferentially about the base so that the micropattern forms a "window pane"-like configuration.

Regarding the material used for the polymeric coating 50, it is important that the material be flexible enough to create an effective interlock with the tissue and be able to withstand the processing for creating the polymer coating 50. Examples of acceptable materials include, but are not limited to, flexible silicones, hydrogels, and other suitable elastomers, such as synthetic rubbers. Other acceptable materials include any flexible, biocompatible, and non-biodegradable polymer. In at least one embodiment, the polymeric coating 50 may include proteins capable of engaging the tissue wall in a biochemical manner. In at least one embodiment, the polymeric coating 50 may include at least one therapeutic agent. In other embodiments, an additional coating may be applied to the polymeric coating 50 that includes a therapeutic agent. A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof.

In a preferred embodiment, the micropillars 54 and the base 56 are formed from the same material. In one or more embodiments, the micropillars 54 are formed from one material and the base 56 is formed from a different material. In one or more embodiments, the micropillars 54 are formed with layers of material, and these layers can be the same material or can be different materials depending on the characteristics required for the desired frictional engagement of the endoprosthesis with the vessel wall. In at least one embodiment, two micropillars 54 of a polymer coating 50 may be formed from the same or different materials.

Because the endoprosthesis 20 has improved frictional engagement with the tissue wall when inserted into a lumen of the patient, removal of the stent may be more difficult with some traditional removal techniques. In at least one embodiment, shown in FIG. 1, the endoprosthesis 20 is provided with a suture or removal loop 55 on one end of the stent. In at least one embodiment, the removal loop 55 is provided on a distal end of the stent. It should be noted that references herein to the term "distal" are to a direction away from an operator of the devices of the present disclosure, while references to the term "proximal" are to a direction toward the operator of the devices of the present disclosure. While sutures or removal loops are well known in the art for removing endoprosthesis, typically sutures or removal loops are provided on the proximal end of the stent, in other words the closest end to the practitioner. Here, the suture or removal loop is applied to the opposite end of the endoprosthesis. In at least one embodiment, the practitioner grabs the loop from inside the endoprosthesis, and by applying an axial force to the loop, the distal end of the endoprosthesis is pulled through the lumen of the endoprosthesis itself. Thus, the micropillars are peeled away from the vessel wall while the stent is flipped inside out to remove the endoprosthesis. In other embodiments, the practitioner may grab the loop from outside the endoprosthesis or at an end of the endoprosthesis.

To manufacture the endoprosthesis 20, several methods can be employed. The polymeric coating 50 can be molded separately from the stent and then adhered to the stent with an adhesive layer 60 between the outer surface of the endoprosthesis and the base of the polymeric coating. Polymeric material can be injected into a mold with the inverse of the micropattern to create the polymeric coating. Also, the polymeric material can be pulled through a mold using a vacuum pump system. In at least one embodiment, the polymeric coating can be created using soft lithography techniques. In one or more embodiments, etching techniques can be used to create the coating, wherein material is taken away from a layer of the coating material to create the micropattern of the polymeric coating 50. In yet another embodiment, a technique called hot embossing can be used, which involves stamping partially cured polymer into the desired shape of the polymeric coating and then curing it before it is applied to the stent. Stamping may or may not include the use of a solvent.

Figure 11:
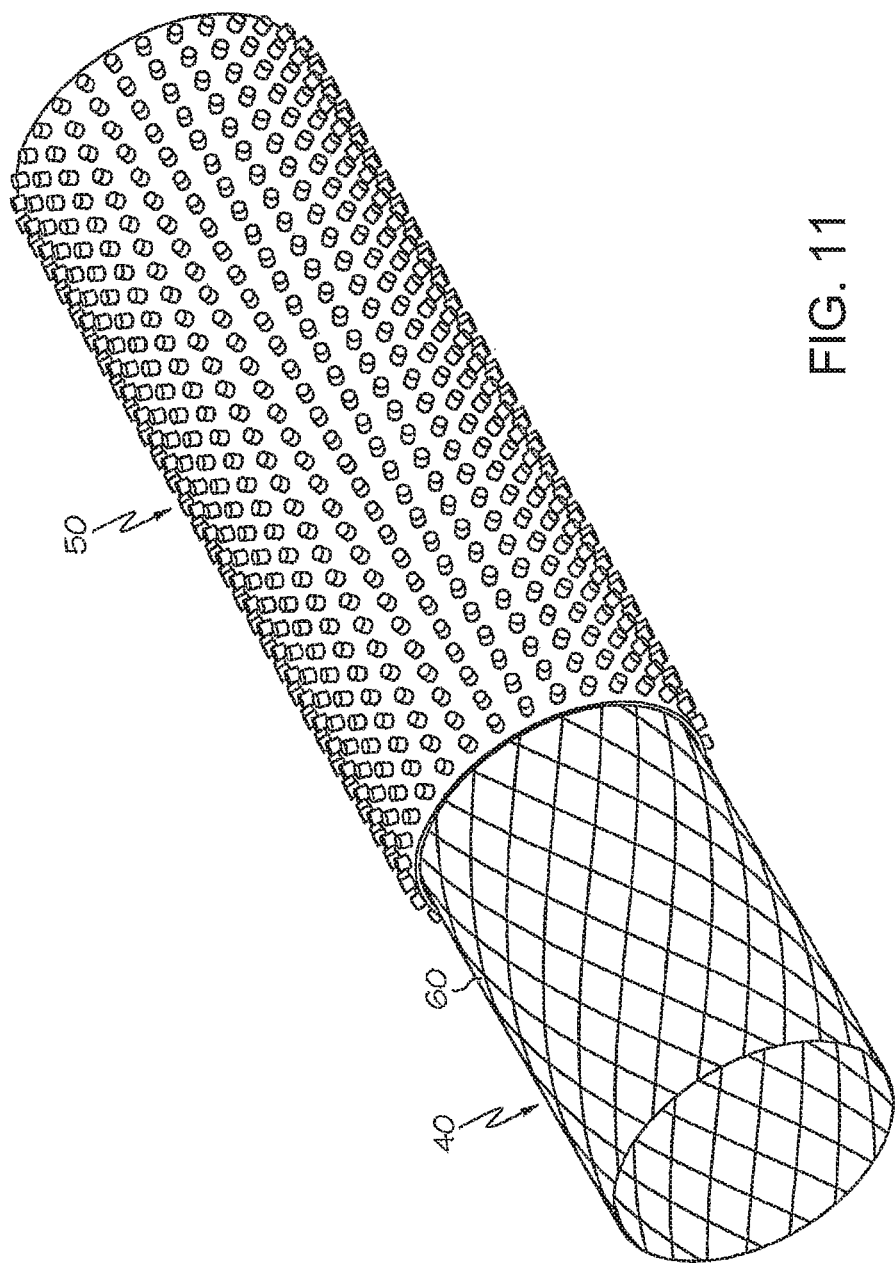
FIG. 11 is a view of the stent and polymeric coating during one method of manufacturing the endoprosthesis.

In at least one embodiment, as shown in FIG. 11, the coating 50 can be molded as a substantially tubular structure with a lumen defined by the base of the coating. An adhesive layer 60 can be applied to either the stent or to at least a portion of the inner surface of the base of the coating. In at least one embodiment, the adhesive layer 60 may substantially cover the entire inner surface of the base of the coating. The stent 40 can be inserted into the lumen of the coating 50. In at least one embodiment, heat and/or pressure may be applied to ensure proper adhesion of the coating 50 to the stent 40 via the adhesive layer 60. The adhesive layer may include silicone coatings, other suitable adhesives, or priming solutions that enable the coating to adhere to the metal stent (or stent coating thereon). In one or more embodiments, as shown in FIG. 12, rather than being molded as a tubular structure, the coating 50 can be molded as a strip attached to the outer surface 44 of the stent 40. In some embodiments, the strip can be applied as perimeter strips attached circumferentially about at least a portion of the circumferential perimeter of the stent. In some embodiments, the strip can be a longitudinal strip attached to the stent in a longitudinal direction. In some embodiments, the stent can be helically wrapped about the stent, as shown in FIG. 12. In some embodiments the coating may be applied as a single strip or as multiple strips. Where the coating is applied as multiple strips, directly adjacent strips may abut one another or may be spaced apart from one another. In at least one embodiment, the strips may be partial tubular structures that extend along the length of the stent but only cover a portion of the circumference of the stent. In some embodiments, a portion of stent 40 may be exposed. An adhesive layer 60 can be applied to either the stent or to at least a portion of the base of the coating. In at least one embodiment, heat and/or pressure may be applied to ensure proper adhesion of the coating 50 to the stent 40 via the adhesive layer 60. In at least one embodiment, discrete micropatterns of micropillars can be formed on and/or attached directly to either the stent 40 or the polymeric coating 50.

In one or more embodiments, the polymeric coating 50 can be formed by dip-coating the stent 40 in the coating material without needing an additional adhesive layer to connect the coating 50 to the stent 40. For instance, the stent 40 can be inserted into a mold, which includes a cavity and a tubular member. The cavity is defined by an inner wall of mold, which is an inverse of the desired micropattern. The stent 40 rests on the tubular member such that the inner surface of the stent is disposed about the tubular member. The mold with the stent 40 can be dipped into the coating material so that the coating material fills the mold and attaches to the stent 40. In some embodiments, temperature changes and/or pressure changes may be applied to the mold to cure the coating material. Once the coating material cures to form the polymer coating 50, the endoprosthesis 20 can be removed from the mold. Alternatively, the polymer coating 50 can be injection molded onto the stent using a similar mold. The coating material is injected into the mold rather than the mold being dipped into the coating material.

Micropatterns of the types described herein may aid in reducing the buildup of granulation tissue at, for example, stent ends. For example, micropatterned polymer coatings (e.g., pads, stent end coverings etc.) may be applied to stents or other devices to reduce or eliminate growth of undesirable granulation tissue. In one or more embodiments, micropatterned polymer coatings may be, for example, specifically designed to cushion the covered portion of the device and promote wound healing through administration of appropriate growth factors and/or facilitation of cell migration across a recurring wounded area. Although not wishing to be bound by theory, it is believed that cells such as fibroblasts, endothelial cells, and muscle cells actively sense both the external loading applied to them (outside-in signaling) and the stiffness of their surroundings (inside-out signaling) and respond to these stimuli with changes in adhesion, proliferation, locomotion, morphology, and synthetic profile. More details regarding this are provided by Throm Quinlan et al., "Combining dynamic stretch and tunable stiffness to probe cell mechanobiology in vitro," PLoS One, 2011; 6(8):e23272, which is incorporated herein by reference in its entirety. Also incorporated by reference in its entirety is Yoon et al., "Passive control of cell locomotion using micropatterns: the effect of micropattern geometry on the migratory behavior of adherent cells," Lab Chip, 2012 Jul. 7; 12(13):2391-2402, which indicates that the amount and gradient of physical spatial cues imposed by changing the width and divergence angle of micropatterns make it possible to control the rate and direction of cell migration in a passive way, the result of which offer a potential for reducing the healing time of open wounds.

In one or more embodiments, a micropatterned structure (e.g., a micropatterned polymer coating 50, a micropatterned stent end covering 50A, 50B, etc.) may be expected to reduce the formation of granulation tissue at or near the stent ends by (1) mechanically stimulating cell migration (due to, for example, micropattern topography) around a wound site; (2) adding a protecting polymer barrier between the stent ends (e.g., stent ends that include wire, etc.) and luminal tissue; and/or (3) potentially administering growth factors and/or proteins to the irritated area in order to promote wound healing. For example, factors could be administered that enhance one or more aspects of wound healing to improve the likelihood of complete healing. In one or more embodiments, factors could be administered that specifically move along the phases of wound healing such that granulation tissue building would be reduced or eliminated (e.g., relative to a similar embodiment without use of the factor, relative to a similar embodiment without the use of a micropatterned stent end covering).

For example, a graphical representation of the cellular characteristics of the wound healing process is presented by de la Torre et al. (de la Torre et al., "Chronic Wounds," MedScape Reference—Drugs, Diseases and Procedures, available at http://emedicine.medscape.com/article/1298452-overview#showall) (last accessed Mar. 7, 2013)), incorporated by reference in its entirety, including different types of cell involvement over the course of wound healing. The progression of specific cell, matrix, or processes each maximize in the following order according to de la Torre et al.: platelets, neutrophilia, macrophagen, lymphocytes, capillaries and epithelium, fibroblasts, and collagen. De la Torre indicates that in the second stage of the inflammatory phase, leukocytes supplant platelets as the dominant cell type, attracted by chemotaxis (chemical signaling through growth factor/protein concentrations). White blood cells are the predominant cells for the first 3 days after wounding and after 24-36 hours, circulating monocytes enter the wound and mature into tissue macrophages. These cells debride the wound on the microscopic level and produce a wide variety of important substances, such as IL-1 and basic fibroblast growth factor (bFGF). IL-1 stimulates the proliferation of inflammatory cells and promotes angiogenesis through endothelial cell replications. bFGF is a chemotactic and mitogenic factor for fibroblasts and endothelial cells. Two to three days after healing, fibroblasts migrate inward from wound margins over the fibrinous matrix established during the inflammatory phase. During the first week, fibroblasts begin producing glycosaminoglycans and proteoglycans, the ground substance for granulation tissue, as well as collagen, in response to macrophage-synthesized bFGF and TGF-β, as well as PDGF (growth factors that influence cell behavior).

In at least one embodiment, a micropatterned structure (e.g., a polymer coating 50, a stent end covering 50A, 50B, etc.), as described herein, may assist with the proliferation and remodeling stages of wound healing, but could also be used to deliver or promote growth factors during the initial inflammatory stage (e.g., if applied early enough and designed to do so).

In at least one embodiment, an endoprosthesis 20 may include a stent having one or more stent ends 46, 48 having a covering 50A (e.g., a stent end covering) attached thereto having a micropatterned surface that may extend circumferentially around at least a portion of a stent end 46 and may optionally extend longitudinally beyond (e.g., cantilever) a stent end 46.

For example, FIGS. 13A-13D depict schematics of a portion of an endoprosthesis 20 having a stent 40 that has a stent end 46 having a covering 50A attached thereto. Covering 50A extends circumferentially around stent end 46 (e.g., FIG. 13C). In one or more embodiments, covering 50A extends circumferentially only partially around stent end 46. As shown, covering 50A may cover the entire area (e.g., the entire circumference of the stent end) around the stent end 46 where, for example, granulation tissue buildup would otherwise be expected.

In some embodiments, the micropatterned covering 50A may extend beyond the end of the endoprosthesis (e.g., extending in the manner of a cantilever). In some embodiments, the micropatterned covering 50A may have a varying radial thickness, which may allow for the covering to double back into the end of the stent, thereby forming a thicker cushion near and around the stent end 46 (e.g., FIG. 13D).

In one or more embodiments, the micropatterned covering may be used at a plurality of stent ends 46, 48 (e.g., both ends of a tubular stent, two or more ends of a bifurcated stent, etc.).

The use of a micropatterned stent end covering 50A as described herein may better protect the ends of the stent (and better protect the luminal tissue near the stent ends) and may promote wound healing. Thus, damaged luminal tissue (e.g., gastrointestinal tissue, tracheal tissue, etc.) may heal properly in a more timely manner, which may reduce excessive growth of delicate granulation tissue.

In one or more embodiments, covering 50A may be applied to any of a wide variety of materials of endoprosthesis construction (e.g., metal, polymer, etc.). In one or more embodiments, a micropatterned covering for use in reduction of granulation tissue growth may be utilized on any of a wide variety of long-term implant devices that may generate granulation tissue by repeated trauma. In one or more embodiments, an endoprosthesis having a micropatterned stent end covering 50A may be placed in, for example, a gastrointestinal tract and its branches (e.g., esophageal, duodenal, biliary, colonic, etc.) or an airway.

FIGS. 13A-13D depict basic schematics of where the micropatterned stent end coverings 50A may be disposed in relation to an endoprosthesis. Covering 50A may include any of the one or more micropatterns described herein and the micropillars of the covering's micropattern may include any of the one or more micropillar structures and dimensions described herein. For example, covering 50A may include one micropattern or a plurality of micropatterns (e.g., having the same or different geometric arrangements, having the same or different density of micropillars per area of base, etc.). Covering 50A may include uniformly shaped and sized micropillars or may include micropillars having two or more shapes and/or two or more dimensions. The microscale features (e.g., micropillars) may take any of a wide variety of forms (e.g., shapes, dimensions) in order to effectively stimulate cells to migrate (or to promote other biological responses (e.g., tasks) that aid in wound healing.

Although ingrowth and granulation tissue buildup is commonly observed near stent ends, the micropatterned coverings 50A of the present disclosure may be disposed in a wide variety of locations along an endoprosthesis. In one or more embodiments, a micropattern used in covering 50A may be applied to other portions of an endoprosthesis (e.g., a medial portion disposed between the stent ends, the perimeter of a radial-facing opening, etc.), if desired.

In at least one embodiment, a stent end covering 50A having a micropatterned surface may be deployed in a body lumen separately from an endoprosthesis, wherein the stent end covering may be deployed in a body lumen followed by deployment of an endoprosthesis wherein a stent end is disposed within at least a portion of the stent end covering (e.g., the stent end covering may be biased between the stent end and the wall of the body lumen).

For example, in FIGS. 14A-14B, micropatterned stent end coverings 50B may take the form of bands (e.g., circular bands, ring-shaped bands, bands having one or more radial thicknesses, etc.) that may be placed with a body lumen before stent deployment (e.g., FIG. 14A), such that the stent ends may be deployed onto the bands (e.g., with the each band disposed between a stent end and the luminal wall). In at least one embodiment, each of two micropatterned stent end coverings 50B may be disposed within a body lumen such that a portion of the body lumen to be stented is located between the micropatterned stent end coverings 50B. A stent may then be disposed within the body lumen such that the respective ends of the stent are deployed onto the micropatterned stent end coverings (e.g., micropatterned pads) as shown in FIG. 14B.

In the one or more embodiments of FIGS. 14A-14B, because the bands are deployed separate from the endoprosthesis, the constraints on design of the band are fewer. That is, the dimensions and/or material properties of each band may be such that delivery while attached to an endoprosthesis is impossible or impractical. For example, the bands depicted in FIGS. 14A-14B may be allowed to be thicker and more effective as protective pads (e.g., relative to the coverings 50A of FIG. 13A, etc.) and need not be deployed with the endoprosthesis through, for example, a sheath delivery system. This embodiment may limit use, however, depending on the anatomy in which the endoprosthesis is deployed (e.g., the anatomy being stented).

Herein, all of the features, qualities, characteristics, functions, and descriptions of polymer coating 50 apply to stent end coverings 50A, 50B, unless the context indicates otherwise.

Stent end coverings 50A, 50B may be manufactured in any of a wide variety of methods including, but not limited to, lithography, etching, and particle deposition.

In one or more embodiments, the stent end covering 50A, 50B may be manufactured separately prior to application (e.g., adherence, attachment, etc.) to a medical device (e.g., stent, etc.). In one or more embodiments, a medical device (e.g., a stent, etc.) may incorporate a micropattern near the ends of the device (e.g., stent ends). For example, in one or more embodiments in which a portion (e.g., an end portion) of a medical device is made of an appropriate material (e.g., silicone, silicone coating, biocompatible polymer or metal, etc.) for micropatterning for reduction of granulation tissue buildup, then the micropattern may be directly incorporated into the structure of the medical device (e.g., stent, etc.).

In one or more embodiments, stent end coverings 50A, 50B may include any of a wide variety of materials of construction including, but not limited to, the materials described herein for bases and/or micropillars, flexible polymers, rigid polymers, biocompatible polymers, metals, and any other suitable material known to one of skill in the art. In some embodiments, a stent end covering may include a material of construction useful for, for example, cell migration and growth factor delivery.

As mentioned herein with regard to FIGS. 9E and 9F, a micropillar 54 may include a tip 55e at or near the end of the protrusion that either softer or more rigid than the remainder of the protrusion (FIG. 9E), a frayed tip 55f (FIG. 9F), and other features that may impart desirable gripping, stiffness, or flexibility characteristics for the endoprosthesis, and any combination of features thereof. The tip 55e may include a different material than the remainder of the protrusion.

In one or more embodiments of the present disclosure, a micropillar 54 may include a tip that includes a hygroscopic material (e.g., a hygroscopic polymer such as nylon, acrylonitrile butadiene styrene (ABS), polycarbonate, cellulose, and poly(methyl methacrylate), etc.) and includes a geometry and/or a material composition that may facilitate anchoring the micropillar in tissue. Anchoring a micropillar in tissue may be useful for reducing or eliminating migration of the micropatterned item.

Figure 15:
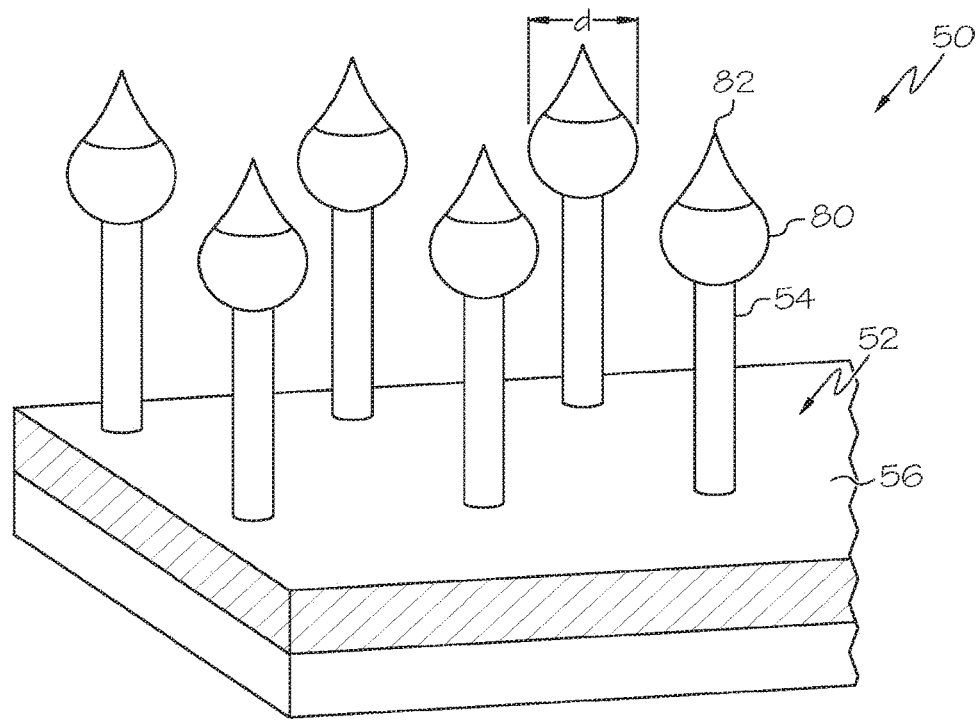
FIG. 15 depicts a perspective view of micropillars having an anchor tip.
Figure 16:
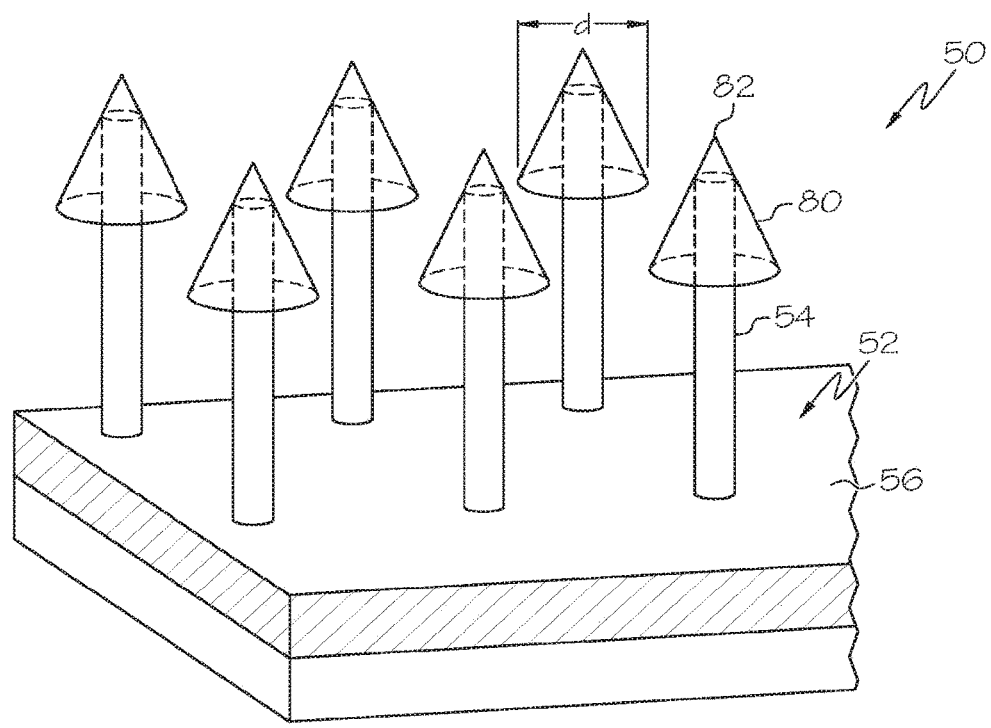
FIG. 16 depicts a schematic of a micropillar having a swellable anchor tip (e.g., before swelling).
Figure 17:
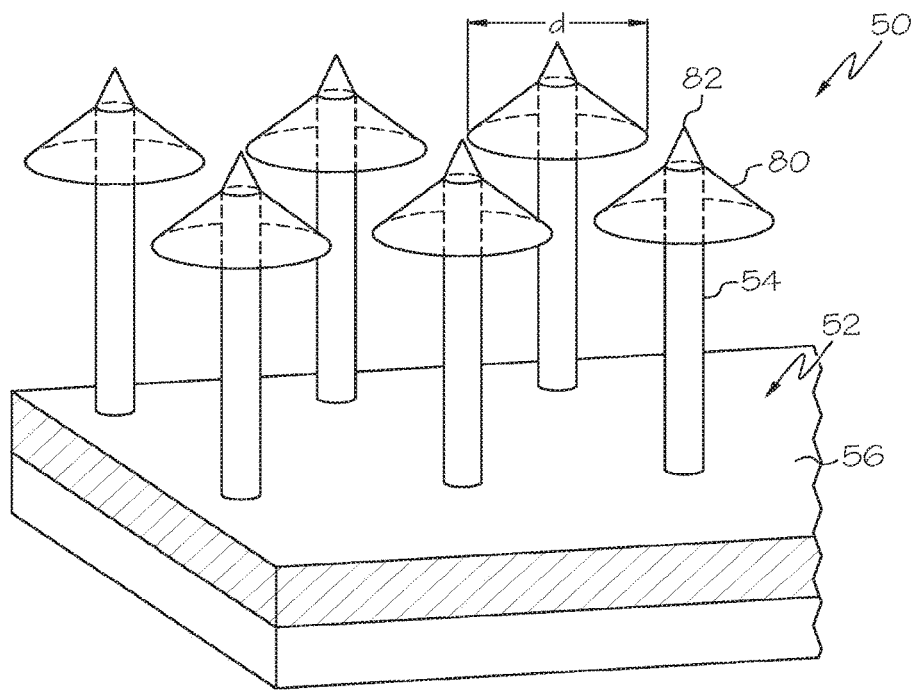
FIG. 17 depicts a schematic of a micropillar having a swellable anchor tip (e.g., after swelling).

As shown in FIGS. 15, 16, and 17, micropillar 54 may include a tip such as an anchor 80 that has a maximum diameter that is larger than the diameter of the micropillar where the micropillar meets the anchor. Anchor 80 may take any of a wide variety of geometries. In one or more embodiments, anchor 80 takes a teardrop shape (e.g., FIG. 15) or a cone shape (e.g., FIGS. 16, 17) having an apex 82 that has a diameter smaller than the diameter of the micropillar where the micropillar meets the anchor.

In one or more embodiments, anchor 80 may be constructed and arranged to penetrate a mucosal membrane with minimal irritation, given the size and aspect ratio of the anchor and micropillar. Once inside the mucosal membrane, the hygroscopic polymer of anchor 80 may absorb surrounding moisture and swell. In at least one embodiment, this increase in diameter will allow micropillars to anchor in the mucosal membrane, which may increase traction and resist migration of the micropatterned polymer coating. For example, in FIGS. 16 and 17, a hygroscopic polymer anchor 80 may have a relatively narrow profile in FIG. 16 which may allow penetration in a mucosal membrane and anchor 80 may have a relatively wide profile in FIG. 17 after the hygroscopic polymer swells. Swelled anchor 80 may then act as a fixation mechanism, such as a barb, to secure the micropillar to the mucosal membrane.

Manufacturing of micropillars 54 having anchors 80 may be accomplished in a wide variety of manners. For example, the micropillars may be cast or molded out of a firm polymer resin to maintain columnar strength, followed by dip coating the micropillars in a hygroscopic polymer to allow a tip (e.g., a fine point tip) to be formed. Other methods of forming a micropillar with an anchor are contemplated.

In one or more embodiments of the present disclosure, a micropatterned polymer coating 50 may be used to provide an adhesive quality to medical devices (e.g., medical devices to treat obesity). A jejunal liner, which may be used to treat obesity, may include a sleeve having an anchor portion (e.g., a flared end, a portion with barbs, etc.) that is anchored in a pylorus and prevents food absorption in the duodenum and part of the jejunum. Jejunal liners may be commercially available from GI Dynamics (Lexington, Mass.). Barbs have been used to anchor a jejunal liner in place. In one or more embodiments, an adhesive micropatterned polymer coating 50 may be used to anchor a sleeve at or near a patient's pylorus and may be used in conjunction with or as an alternative to barbs. At least a portion of an outer surface of a jejunal liner sleeve may be covered with an adhesive micropatterned polymer coating 50.

Various portions of a jejunal liner may include an adhesive micropatterned polymer coating 50. For example, an adhesive micropatterned polymer coating 50 may cover an entire outside surface of the sleeve (e.g., wherein the liner lacks an anchor portion and the sleeve is to be adhered to the duodenum and jejunum, etc.), may cover an entire outside surface of an anchor portion (e.g., a flared portion of the sleeve), may cover all or a portion of a sleeve anchored in the esophagus, may cover a sleeve having a stent thereon, may cover a portion of the outside surface of the sleeve (e.g., wherein the sleeve is otherwise adhered to the small intestine with a balloon, etc.). In one or more embodiments, a sleeve having a micropatterned polymer coating 50 thereon (e.g., for anchoring) may be implanted distal of the papilla of Vaters.

The micropatterned polymer coatings 50 of the present disclosure may be utilized on any of a wide variety of medical devices (e.g., for treating obesity, etc.). For example, stents have been used for treating leaks after bariatric surgery. In one or more embodiments, a stent (or a portion thereof) may have an adhesive micropatterned polymer coating 50 thereon, which may reduce or prevent migration (e.g., of the stent). In one or more embodiments, gastric banding may include an adhesive micropatterned polymer coating 50 thereon to reduce or prevent migration.

Another aspect of the present disclosure relates to a patch, e.g., for the treatment of a wound. In one or more embodiments, a wound patch may include one or more polymer coatings (e.g., micropatterned polymer coatings) that may facilitate wound healing. In at least one embodiment, wound patches may be utilized in a body lumen (e.g., gastrointestinal tissue).

Figure 18:
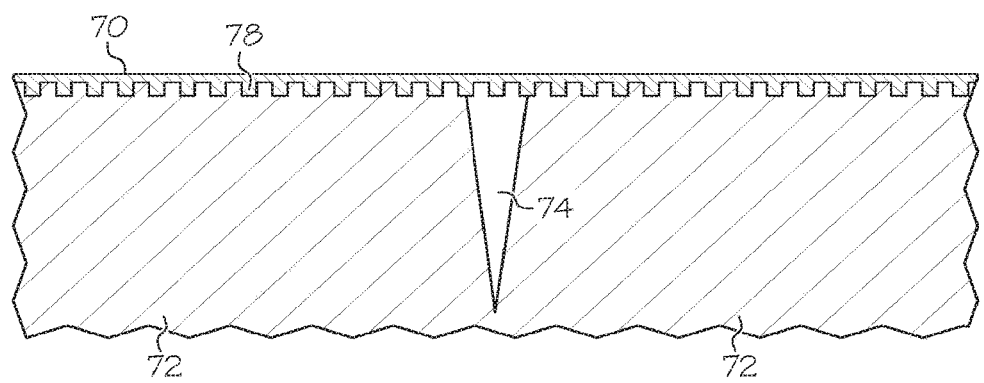
FIG. 18 depicts a schematic of a wound patch (including one or more micropatterns) placed over a wound.

With reference to FIG. 18, a micropatterned wound patch 70 may be adhered to tissue 72 (e.g., a gastrointestinal wall, etc.) near to and/or circumscribing a wound site 74. Wound patches of the present disclosure may be useful for wound sites in any portion of a body (e.g., body lumen, skin, body cavity, etc.).

In one or more embodiments, a wound patch 70 may include one or more adhesive micropatterned polymer coatings 76 on the edges of the wound patch 70, wherein the micropatterned polymer coatings 76 are configured and arranged to adhere to gastrointestinal (GI) tissue 72. In one or more embodiments, a wound patch 70 can take any of a wide variety of shapes and can be structured such that the micropatterned polymer coatings 76 for adhering to tissue 72 are arranged on, for example, at least two sides of a wound site 74. That is, the adhesive micropatterned polymer coating 76 may form a type of perimeter, or portion thereof, that extends entirely or partially around a wound site 74. In at least one embodiment, the adhesive micropatterned polymer coating 76 holds the wound patch 70 in place over the wound (e.g., the wound patch extends over the wound site 74) during the healing process, thereby preventing the wound patch 70 from being dislodged within the GI tract as well as protecting the wound 74 from any detrimental effects present in the GI environment. In at least one embodiment, a wound patch 70 can hold the tissue of a wound 74 closer together (e.g., help close the wound) during healing, which may reduce the time required for healing.

Many configurations of one or more micropatterned polymer coatings on a wound patch are envisioned in the present disclosure. For example, in FIGS. 19A-19C, three examples of micropattern arrangements are provided. For each wound patch 70 depicted, one or more adhesive micropatterned polymer coatings 76 are arranged on or near one or more edges of the wound patch 70. A plurality of adhesive micropatterned polymer coatings 76 may be arranged along a perimeter of a wound patch 70, a continuous adhesive micropatterned polymer coating 76 may extend around the entire perimeter of a wound patch 70, or two adhesive micropatterned polymer coatings 76 may be disposed on at least two ends/edges of a wound patch 70. Many other arrangements are possible and may be envisioned by one of skill in the art.

In one or more embodiments, a region of a wound patch 70 to be located directly over a wound 74 may also include a wound-covering micropatterned polymer coating 78, in at least one embodiment. For example, a micropatterned polymer coating may include a micropattern that can promote cell migration. Stimulation of tissue of the wound site 74 by the micropattern may result in a higher cell count at the wound site 74, which can expedite healing in at least one embodiment. In one or more embodiments, the wound-covering micropatterned polymer coating 78 over the wound site 74 may be structured and arranged to control other aspects of cell behavior by, for example, releasing growth factors, releasing therapeutic agents, releasing proteins, etc. In some embodiments, the micropatterned polymer coating 78 disposed over a wound site 74 may include the same micropattern (e.g., the same micropillar area density, micropillar geometric arrangement/pattern, micropillar dimensions, micropillar shape, micropillar composition, etc.) as the adhesive micropatterned polymer coating 76 used for adhesion to tissue. In one or more embodiments, these micropatterns 76, 78 may differ in one or more ways (e.g., area density, pattern, dimensions, shape, composition, etc.), without limitation.

Figure 19A:
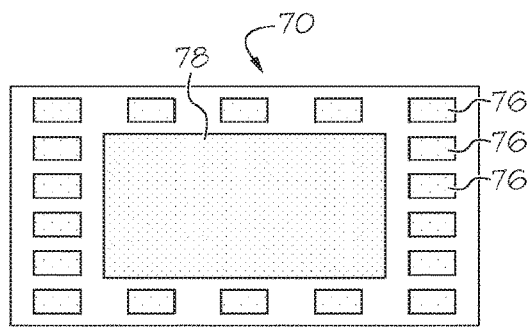
FIGS. 19A-19C depict three example wound patches, each having a different arrangement of adhesive micropatterned polymer coating(s) and wound-covering micropatterned polymer coating(s).
Figure 19B:
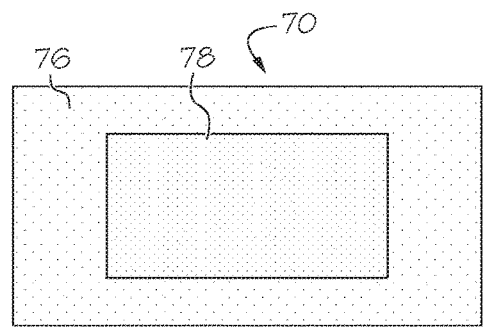
Figure 19C:
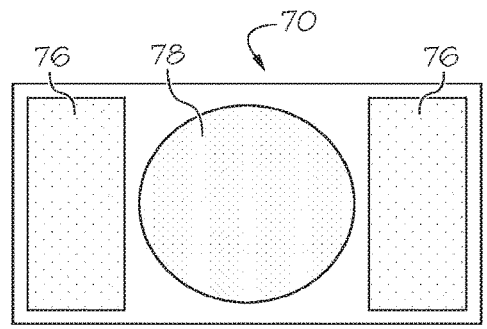

Also depicted in the examples of micropattern arrangements in FIGS. 19A-19C are wound-covering micropatterned polymer coatings 78, which can take any shape (e.g., geometric, non-geometric, etc.) in at least one embodiment. Each of the wound patches 70 of FIGS. 19A-19C includes one wound-covering micropatterned polymer coating 78, but a plurality of wound-covering micropattern polymer coatings 78 can be used in one or more embodiments. Many other arrangements of wound-covering micropatterned polymer coatings may be envisioned by one of skill in the art.

In one or more embodiments, a wound patch 70 can include one or more radiopaque portions (e.g., markers) for improved visualization (e.g., via fluoroscopy, etc.), improved positioning accuracy during delivery, and/or improved monitoring after delivery. Each radiopaque marker can be disposed at a strategic location on a wound patch 70 depending on the wound patch geometry and target wound site anatomy and would be viewable before, during, and after the wound patch deployment procedure.

In one or more embodiments, a plurality of wound patches 70 can be used to achieve increased tissue adhesion and/or increased cell stimulation.

A wound patch 70 that includes one or more micropatterned polymer coatings 76, 78 may be useful in a wide variety of applications including treatment of post-biopsy bleeding, ulcers, variceal bleeding, fistula, etc.

Figure 20A:
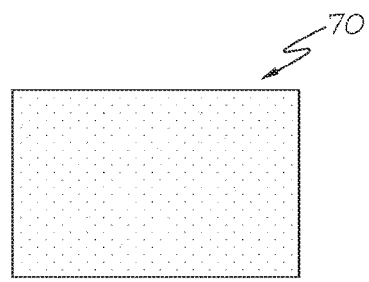
FIGS. 20A-20C depicts a schematic of the method of deploying a wound patch using a tubular delivery system, such as an endoscope.
Figure 20B:
Figure 20C:
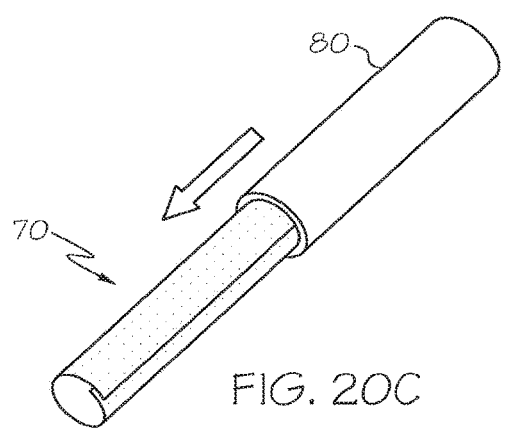

Deployment of a wound patch 70 of the present disclosure may be accomplished in any of a wide variety of ways. As depicted in FIGS. 20A-20C, in one or more embodiments, a wound patch 70 (e.g., FIG. 20A) can be rolled (e.g., FIG. 20B) and placed within a delivery system (e.g., an endoscopic delivery system, a TTS delivery system, etc.), and deployed through an endoscope 80 for use in a body lumen (e.g., GI tract). A rolled wound patch 70 may be advanced through an endoscope 80 using, e.g., a pusher or plunger. When the wound patch 70 is in place (confirmed by, for example, fluoroscopy), the rolled wound patch 70 may be pushed forward (distally) or the endoscope may be pulled backward (proximally) to deploy the wound patch 70 (e.g., FIG. 20C).

In one or more embodiments, a wound patch 70 may be rolled around an expansive or inflatable mandrel or balloon within a delivery system, wherein the mandrel or balloon would press the wound patch 70 against the tissue 72 (e.g., GI wall) upon or after deployment to initiate adhesion of the adhesive micropatterned polymer coating 76 to the tissue 72 (e.g., GI wall).

In one or more embodiments, the wound patch 70 can include a wide variety of materials of construction, including flexible polymers, woven mesh, etc. The micropatterned polymer coatings 76, 78 on wound patches 70 may be made from any of a wide variety of materials in order to provide an effective structure for tissue adhesion and cell migration including, but not limited to, those materials identified herein with regard to polymer coating 50. The micropatterned polymer coatings may be manufactured in any of the ways described herein with regard to other micropatterned polymer coatings. In one or more embodiments, a wound patch 70 can include a separate backing with micropatterned polymer coatings 76, 78 attached thereto. In one or more embodiments, the wound patch 70 can be an integral piece of material having micropatterns formed thereon or incorporated therein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the present disclosure such that the present disclosure should be recognized as also specifically directed to other embodiments having any other possible combination of the features of the dependent claims.

A description of some exemplary embodiments of the invention is contained in one or more of the following numbered statements:

Statement 1. An endoprosthesis having an expanded state and an unexpanded state, the endoprosthesis comprising:
  a stent, wherein the stent has a first end, a second end, an inner surface extending from the first end to the second end and defining a lumen, an outer surface extending from the first end to the second end, and a thickness defined between the inner surface and the outer surface; and a stent end covering disposed at one of the first and second ends, the stent end covering comprising:
a polymeric coating comprising a base and a plurality of protrusions, the base comprising a first major surface facing the outer surface of the stent, the base further comprising a second major surface from which each of the plurality of protrusions extends outwardly, the first major surface opposing the second major surface, wherein the protrusions are arranged in a micropattern.

Statement 2. The endoprosthesis of statement 1, wherein the stent end covering is adhered to the outer surface of the stent.

Statement 3. The endoprosthesis of statement 1 or statement 2, wherein the stent end covering is adhered to the inner surface of the stent.

Statement 4. The endoprosthesis of any one of statements 1-3, wherein the stent end covering extends circumferentially and entirely around one of the first and second ends.

Statement 5. The endoprosthesis of any one of statements 1-4, wherein the stent end covering extends circumferentially and partially around one of the first and second ends.

Statement 6. The endoprosthesis of any one of statements 1-5, wherein the stent end covering extends longitudinally from a location between the first and second ends to a location that is not between the first and second ends.

Statement 7. The endoprosthesis of any one of statements 1-6, wherein at least a first portion of the stent end covering has a radial thickness greater than the thickness of the stent at the stent end that is nearest to the stent end covering.

Statement 8. The endoprosthesis of statement 7, wherein at least a second portion of the stent end covering has a radial thickness less than the radial thickness of the first portion of the stent end covering.

Statement 9. The endoprosthesis of any one of statements 1-8, wherein the stent end covering comprises:
a first stent end covering and a second stent end covering, wherein one of the first and second stent end coverings is disposed at the first end and one of the first and second stent end coverings is disposed at the second end.

Statement 10. A method of manufacturing an endoprosthesis comprising:
forming a stent end covering comprising a polymeric coating, wherein the polymeric coating comprises a base and a plurality of protrusions, the base comprising a first major surface facing the outer surface of the stent, the base further comprising a second major surface from which each of the plurality of protrusions extends outwardly, the first major surface opposing the second major surface, wherein the protrusions are arranged in a micropattern;
providing a stent having a first end, a second end, an inner surface extending from the first end to the second end and defining a lumen, an outer surface extending from the first end to the second end, and a thickness defined between the inner surface and the outer surface; and
contacting the stent end covering with one of the first and second ends of the stent.

Statement 11. The method of statement 10, wherein the contacting further comprises contacting the stent end covering with the outer surface of the stent.

Statement 12. The method of statement 10 or statement 11, wherein the contacting further comprises contacting the stent end covering with the inner surface of the stent.

Statement 13. The method of any one of statements 10-12, wherein the contacting comprises disposing the stent end covering circumferentially and entirely around one of the first and second ends.

Statement 14. The method of any one of statements 10-13, wherein the contacting comprises disposing the stent end covering wherein the stent end covering extends longitudinally from a location between the first and second ends to a location that is not between the first and second ends.

Statement 15. The method of any one of statements 10-14, wherein the method further comprises:
disposing the stent end covering within a body lumen, wherein disposing the stent end covering within the body lumen occurs before contacting the stent end covering with one of the first and second ends of the stent.

Statement 16. The method of any one of statements 10-15, wherein the contacting comprises deploying the stent within the body lumen, wherein the stent end covering is disposed between a lumen wall of the body lumen and one of the first and second ends of the deployed stent.

Statement 17. The method of any one of statements 10-16, wherein forming the stent end covering comprising the polymeric coating comprises using a mold having an inverse of the micropattern and injecting a polymeric material into the mold.

Statement 18. The method of any one of statements 10-17, wherein the contacting comprises applying an adhesive to at least one of a surface of the base and the outer surface of the stent.

Statement 19. A method of using an endoprosthesis comprising:
providing a stent end covering comprising a polymeric coating, wherein the polymeric coating comprises a base and a plurality of protrusions, the base comprising a first major surface facing the outer surface of the stent, the base further comprising a second major surface from which each of the plurality of protrusions extends outwardly, the first major surface opposing the second major surface, wherein the protrusions are arranged in a micropattern;
providing a stent having a first end, a second end, an inner surface extending from the first end to the second end and defining a lumen, an outer surface extending from the first end to the second end, and a thickness defined between the inner surface and the outer surface; and
disposing the stent end covering within a lumen; and
after disposing the stent end covering within a lumen, contacting the stent end covering with one of the first and second ends of the stent.

Statement 20. The method of statement 19, wherein the contacting comprises deploying a stent within the lumen.

This completes the description of the preferred and alternate embodiments of the present disclosure. Those skilled in the art may recognize other equivalents to the specific embodiment described herein which equivalents are intended to be encompassed by the claims attached hereto.

The invention claimed is:

1. An endoprosthesis having an expanded state and an unexpanded state, the endoprosthesis comprising:
a stent having an inner surface and an outer surface; and
a stent covering disposed on at least a portion of the outer surface of the stent, the stent covering including a polymeric coating having a base and a plurality of protrusions extending outwardly from the base, wherein the protrusions include a firm polymer resin columnar portion and a hygroscopic polymer coating, wherein the protrusions are arranged in a micropattern, wherein the protrusions are configured to expand from a first profile to a second profile.

2. The endoprosthesis of claim 1, wherein a diameter of each of the protrusions in the second profile is larger than a diameter of the protrusions in the first profile.

3. The endoprosthesis of claim 1, wherein the protrusions are configured to move from the first profile to the second profile when the protrusions are placed in a moist environment.

4. The endoprosthesis of claim 1, wherein the columnar portions of the protrusions extend from the base and a tip portion is disposed on each columnar portion, wherein a diameter of the tip portion is greater than a diameter of the columnar portion in the second profile.

5. The endoprosthesis of claim 4, wherein the tip portions are cone shaped.

6. The endoprosthesis of claim 1, wherein the stent covering extends over an entirety of the outer surface of the stent.

7. The endoprosthesis of claim 1, wherein the stent extends along a longitudinal axis from a first end to a second end, the stent having a middle portion between the first and second ends, wherein the stent covering extends over one or both of the first and second ends, but not the middle portion.

8. The endoprosthesis of claim 7, wherein the stent covering extends longitudinally beyond the first or second ends of the stent.

9. The endoprosthesis of claim 8, wherein the stent covering doubles back into a lumen of the stent.

10. The endoprosthesis of claim 1, wherein the stent covering is adhered to the outer surface of the stent.

11. An endoprosthesis having an expanded state and an unexpaned state, the endoprosthesis comprising:
   a tubular stent, wherein the stent has an inner surface, an outer surface, a first end, a second end, and a thickness defined between the inner surface and the outer surface, wherein the stent has a plurality of openings extending through the thickness; and
   a polymeric coating adhered to the outer surface of the stent, the polymeric coating comprising a base and a plurality of protrusions extending outwardly from the base, each protrusion having a columnar portion extending from the base and a distal tip portion disposed on the columnar portion, wherein the columnar portion is made of a first material and the distal tip portion is made of a second material different from the first material, wherein the protrusions are arranged in a micropattern, wherein the base covers the openings of the stent; wherein the distal tip portions of the protrusions are configured to expand from a first profile to a second profile.

12. The endoprosthesis of claim 11, wherein a diameter of the distal tip portion of each of the protrusions in the second profile is larger than a diameter of the protrusions in the first profile.

13. The endoprosthesis of claim 11, wherein the protrusions are configured to move from the first profile to the second profile when the protrusions are placed in a moist environment.

14. The endoprosthesis of claim 11, wherein the protrusions include a hygroscopic polymer.

15. The endoprosthesis of claim 14, wherein the columnar portions of the protrusions include a firm polymer resin and the distal tip portions include a hygroscopic polymer coating.

16. An endoprosthesis having an expanded state and an unexpanded state, the endoprosthesis comprising:
   a tubular stent having an inner surface and an outer surface; and
   a stent covering disposed on at least a portion of the outer surface of the stent, the stent covering including a polymeric coating having a base and a plurality of protrusions extending outwardly from the base, wherein the protrusions include a firm polymer resin columnar portion and a hygroscopic polymer coating, wherein the protrusions are arranged in a micropattern.

* * * * *